(12) United States Patent
Inoue et al.

(10) Patent No.: US 9,916,963 B2
(45) Date of Patent: Mar. 13, 2018

(54) SPECIMEN LOADING METHOD, SPECIMEN STAGE, AND CHARGED PARTICLE BEAM DEVICE

(71) Applicant: JEOL Ltd., Tokyo (JP)

(72) Inventors: Noriyuki Inoue, Tokyo (JP); Yoshiko Takashima, Tokyo (JP)

(73) Assignee: JEOL Ltd., Tokyo (JP)

( * ) Notice: Subject to any disclaimer, the term of this patent is extended or adjusted under 35 U.S.C. 154(b) by 0 days.

(21) Appl. No.: 15/320,912

(22) PCT Filed: Jun. 18, 2015

(86) PCT No.: PCT/JP2015/067646
§ 371 (c)(1),
(2) Date: Dec. 21, 2016

(87) PCT Pub. No.: WO2015/198968
PCT Pub. Date: Dec. 30, 2015

(65) Prior Publication Data
US 2017/0154753 A1    Jun. 1, 2017

(30) Foreign Application Priority Data

Jun. 27, 2014  (JP) ................................ 2014-132377
May 15, 2015  (JP) ................................ 2015-100252

(51) Int. Cl.
*G01F 23/00*       (2006.01)
*H01J 37/20*       (2006.01)
(Continued)

(52) U.S. Cl.
CPC ............... *H01J 37/20* (2013.01); *G01N 1/36* (2013.01); *H01J 37/16* (2013.01); *H01J 2237/2007* (2013.01); *H01J 2237/2801* (2013.01)

(58) Field of Classification Search
CPC .. H01J 37/16; H01J 37/20; H01J 37/26; H01J 37/261
(Continued)

(56) References Cited

U.S. PATENT DOCUMENTS

2008/0308743 A1* 12/2008 Mizuochi ................ H01J 37/20
                                                              250/440.11
2010/0096549 A1*  4/2010 Nishiyama ......... G01N 23/2251
                                                              250/307
(Continued)

FOREIGN PATENT DOCUMENTS

JP          850875 A     2/1996
JP        10241620 A     9/1998
(Continued)

OTHER PUBLICATIONS

ISR re PCT/JP2015/067646 dated Jul. 21, 2015.

*Primary Examiner* — Jason McCormack
(74) *Attorney, Agent, or Firm* — The Webb Law Firm

(57) ABSTRACT

A specimen loading method for loading a specimen that contains water into a specimen chamber of a charged particle beam device, includes: a step (S100) of mounting the specimen on a specimen support; a step (S102) of covering a predetermined area of the specimen with a water retention material; a step (S104) of evacuating the specimen chamber in which the specimen having the predetermined area covered with the water retention material is placed; and a step (S106) of exposing the predetermined area covered with the water retention material.

11 Claims, 21 Drawing Sheets

(51) Int. Cl.
  *G01N 1/36* (2006.01)
  *H01J 37/16* (2006.01)
(58) Field of Classification Search
  USPC ............... 250/306, 307, 311, 442.11, 440.11
  See application file for complete search history.

(56) References Cited

U.S. PATENT DOCUMENTS

| | | | | |
|---|---|---|---|---|
| 2011/0217619 A1* | 9/2011 | Yoshie | ............... | H01M 8/028 |
| | | | | 429/482 |
| 2013/0082190 A1* | 4/2013 | Momoi | ............... | H01J 37/20 |
| | | | | 250/442.11 |
| 2014/0227734 A1* | 8/2014 | Hariyama | ............ | G01N 23/225 |
| | | | | 435/29 |

FOREIGN PATENT DOCUMENTS

| | | |
|---|---|---|
| JP | 2002214091 A | 7/2002 |
| JP | 201055988 A | 3/2010 |
| JP | 201486250 A | 5/2014 |

* cited by examiner

SPECIMEN LOADING METHOD, SPECIMEN STAGE, AND CHARGED PARTICLE BEAM DEVICE

CROSS-REFERENCE TO RELATED APPLICATIONS

This application is the United States national phase of International Application No. PCT/JP2015/067646 filed Jun. 18, 2015, and claims priority to Japanese Patent Application Nos. 2014-132377 and 2015-100252 filed Jun. 27, 2014, and May 15, 2015, respectively, the disclosures of which are hereby incorporated in their entirety by reference.

TECHNICAL FIELD

The present invention relates to a specimen loading method, a specimen stage, and a charged particle beam device.

BACKGROUND ART

A water-containing specimen is normally observed using a scanning electron microscope (SEM) in a state in which the water-containing specimen has been frozen. In this case, however, the original state of the specimen may not be observed since the water contained in the specimen is not present in the form of a liquid.

In order to observe the original state of a water-containing specimen, it is necessary to keep the water contained in the specimen in a liquid phase. In order to keep the water contained in the specimen in a liquid phase when observing the specimen using a low-vacuum-mode scanning electron microscope, it is necessary to maintain the pressure inside the specimen chamber at about 650 Pa, and maintain the temperature of the specimen at 0° C. to 1° C.

However, when a water-containing specimen that is observed using a scanning electron microscope is loaded directly into the specimen chamber, evaporation of water may occur (i.e., the specimen may dry) during an evacuation step that is performed to achieve the observation conditions. Moreover, the temperature of the specimen may decrease due to heat of evaporation that is generated when the water evaporates from the specimen, whereby the specimen may freeze.

For example, Patent Literature 1 discloses a scanning electron microscope that includes a microinjection device that supplies a trace amount of liquid through a thin tube that is provided from the wall of the specimen chamber to the specimen stage. It is possible to prevent a situation in which the specimen dries by utilizing the scanning electron microscope disclosed in Patent Literature 1. However, since it is necessary to provide the thin tube that connects the inside and the outside of the specimen chamber, the device configuration necessarily becomes complex.

CITATION LIST

Patent Literature

Patent Literature 1: JP-A-10-241620

SUMMARY OF INVENTION

Technical Problem

The invention was conceived in view of the above problem. An object of several aspects of the invention is to provide a specimen loading method and a specimen stage that can prevent a situation in which the specimen dries when loaded into a specimen chamber of a charged particle beam device. Another object of the several aspects of the invention is to provide a charged particle beam device that includes the specimen stage.

Solution to Problem (1) According to one aspect of the invention, there is provided a specimen loading method for loading a specimen that contains water into a specimen chamber of a charged particle beam device, the specimen loading method including:

a step of mounting the specimen on a specimen support;

a step of covering a predetermined area of the specimen with a water retention material;

a step of evacuating the specimen chamber in which the specimen having the predetermined area covered with the water retention material is placed; and a step of exposing the predetermined area covered with the water retention material.

According to the specimen loading method, since the step of evacuating the specimen chamber is performed in a state in which the predetermined area of the specimen is covered with the water retention material, it is possible to reduce evaporation of water from the specimen. Therefore, the specimen loading method can prevent a situation in which the specimen dries when loading the specimen into the specimen chamber. The specimen loading method can also prevent a situation in which the specimen freezes due to heat of evaporation.

(2) In the specimen loading method, the step of exposing the predetermined area may include exposing the predetermined area by moving the specimen and the water retention material relative to each other.

This makes it possible to easily expose the predetermined area of the specimen.

(3) In the specimen loading method, the step of exposing the predetermined area may include exposing the predetermined area by moving the specimen support.

(4) In the specimen loading method, the step of exposing the predetermined area may include exposing the predetermined area by moving the water retention material.

(5) In the specimen loading method, the step of evacuating the specimen chamber may include cooling the specimen.

This makes it possible to keep the water contained in the specimen in a liquid phase as compared with the case where the specimen is not cooled, even when the pressure inside the specimen chamber has been reduced, for example.

(6) The specimen loading method may further include a step of placing the water retention material in a water retention material chamber that is connected to the specimen chamber through a gate valve, after the step of exposing the predetermined area.

When the specimen loading method includes the step of placing the water retention material in the water retention material chamber that is connected to the specimen chamber through the gate valve, it is possible to prevent a situation in which water that has evaporated from the water retention material is supplied to the specimen during observation or analysis.

(7) The specimen loading method may further include a step of moving the water retention material from the water retention material chamber to the specimen chamber, and evaporating water from the water retention material in the specimen chamber to supply the water to the specimen.

This makes it possible to supply water to the specimen during observation or analysis.

(8) The specimen loading method may further include a step of placing the water retention material in a container within the specimen chamber, after the step of exposing the predetermined area.

When the specimen loading method includes the step that places the water retention material in the container within the specimen chamber, it is possible to prevent a situation in which water that has evaporated from the water retention material is supplied to the specimen during observation or analysis.

(9) According to another aspect of the invention, there is provided a specimen stage that is used for a charged particle beam device, the specimen stage including:

a specimen support that supports a specimen;

a holder that can hold a water retention material that covers a predetermined area of the specimen; and a moving mechanism that moves the specimen support or the holder.

According to the specimen stage, the predetermined area of the specimen that has been covered with the water retention material can be exposed by moving the specimen support or the holder using the moving mechanism. Therefore, the specimen stage can reduce evaporation of water from the specimen, and prevent a situation in which the specimen dries or freezes when the specimen is loaded into the specimen chamber by covering the predetermined area of the specimen with the water retention material, and can expose the predetermined area of the specimen when the specimen is observed or analyzed.

(10) According to another aspect of the invention, there is provided a specimen stage that is used for a charged particle beam device, the specimen stage including:

a specimen support that supports a specimen;

a moving mechanism that moves the specimen support; and a restriction section that restricts movement of a water retention material along with movement of the specimen support, the water retention material covering a predetermined area of the specimen.

Since the specimen stage is configured so that the movement of the water retention material (that covers the predetermined area of the specimen) along with the movement of the specimen support can be restricted by the restriction section, the predetermined area of the specimen that has been covered with the water retention material can be exposed. Therefore, the specimen stage can prevent a situation in which the specimen dries or freezes when the specimen is loaded into the specimen chamber by covering the predetermined area of the specimen with the water retention material, and can expose the predetermined area of the specimen when the specimen is observed or analyzed.

(11) According to another aspect of the invention, there is provided a charged particle beam device including the specimen stage.

Since the charged particle beam device includes the specimen stage, it is possible to prevent a situation in which the specimen dries or freezes when the specimen is loaded into the specimen chamber of the charged particle beam device. Therefore, the charged particle beam device makes it possible to observe or analyze the specimen (water-containing specimen) in a state in which the specimen contains water while preventing a situation in which the specimen dries or freezes.

(12) According to a further aspect of the invention, there is provided a charged particle beam device including:

the specimen stage; and a water retention material chamber that is connected to a specimen chamber through a gate valve, and can hold the water retention material, the specimen being loaded into the specimen chamber.

Since the charged particle beam device includes the water retention material chamber that is connected to the specimen chamber through the gate valve, and can hold the water retention material, it is possible to prevent a situation in which water that has evaporated from the water retention material is supplied to the specimen during observation or analysis. According to the charged particle beam device, it is possible to supply water to the specimen at the desired timing, and adjust the amount of water supplied to the specimen by operating the gate valve.

DESCRIPTION OF EMBODIMENTS

The exemplary embodiments of the invention are described in detail below with reference to the drawings. Note that the following exemplary embodiments do not unduly limit the scope of the invention as stated in the claims. Note also that all of the elements described below should not necessarily be taken as essential elements of the invention.

1. First Embodiment 1.1. Specimen Stage

Figure 1:
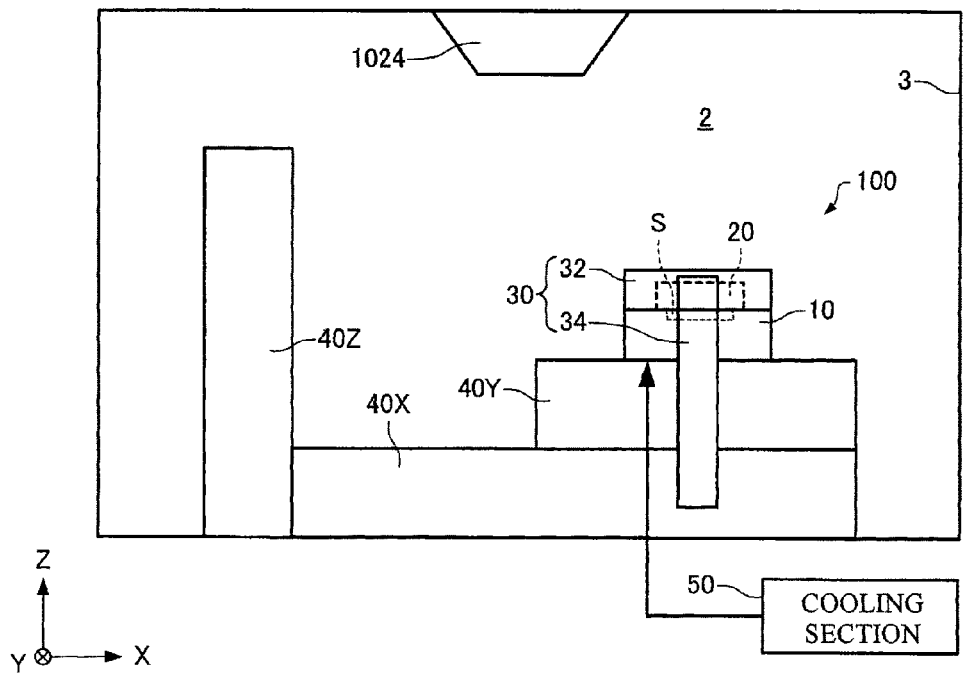
FIG. 1 is a schematic view illustrating the configuration of a specimen stage according to the first embodiment.
Figure 2:
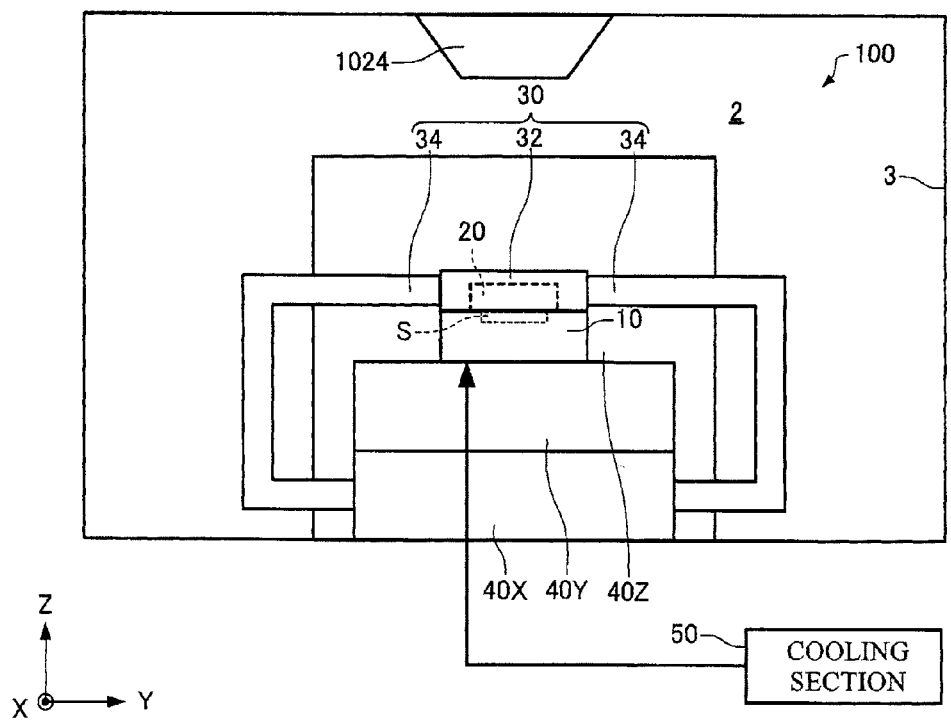
FIG. 2 is a schematic view illustrating the configuration of a specimen stage according to the first embodiment.

A specimen stage according to a first embodiment of the invention is described below with reference to the drawings. FIGS. 1 and 2 are schematic views illustrating the configuration of a specimen stage 100 according to the first embodiment. Note that FIGS. 1 and 2 illustrate a state in which the specimen stage 100 is placed in a specimen chamber 2 of a scanning electron microscope. The X-axis, the Y-axis, and the Z-axis illustrated in FIGS. 1 and 2 are three axes that are orthogonal to each other.

The specimen stage 100 is a specimen stage that is used for a scanning electron microscope. The scanning electron microscope is a device that is used to observe and analyze a specimen S that is supported on a specimen support 10 of the specimen stage 100 by applying an electron beam to the specimen S.

The specimen stage 100 is placed in the specimen chamber 2 of the scanning electron microscope. The specimen chamber 2 is a space in which the specimen S is placed. The specimen chamber 2 is surrounded by a wall 3. The specimen chamber 2 is evacuated by an evacuation device (not illustrated in the drawings) so as to be maintained under a specific pressure (e.g., 650 Pa). An electron beam emitted from an electron optical system that includes an electron beam source 1010, a condenser lens 1022, an objective lens 1024, a scanning deflector 1030 (see FIG. 19 described later), and the like is applied to the specimen S that is supported on the specimen support 10 inside the specimen chamber 2. Note that the constituent members of the scanning electron microscope other than the specimen stage 100 and the objective lens 1024 are omitted in FIGS. 1 and 2.

The specimen S is a water-containing specimen. The term "water-containing specimen" refers to a specimen that contains water. Examples of the specimen S include a living organism, a plant, a food, a cosmetic preparation, and the like. Specific examples of the specimen S include a seaweed (e.g., tangle weed), konjac, agar, a water-absorbing polymer, a contact lens, a lipid, and the like.

As illustrated in FIGS. 1 and 2, the specimen stage 100 includes the specimen support 10, a water retention material 20, a holder 30, an X moving mechanism 40X, a Y moving mechanism 40Y, a Z moving mechanism 40Z, and a cooling section 50.

The specimen support 10 supports the specimen S. The specimen support 10 is a plate-like member, for example. The specimen S is placed on the specimen support 10. The specimen S is secured on the specimen support 10. The specimen support 10 is provided on the Y moving mechanism 40Y.

The specimen support 10 can be moved in the X-axis direction by operating the X moving mechanism 40X. The specimen support 10 can be moved in the Y-axis direction by operating the Y moving mechanism 40Y. The specimen support 10 can also be moved in the Z-axis direction by operating the Z moving mechanism 40Z. The specimen S supported on the specimen support 10 moves along with the movement of the specimen support 10.

The water retention material 20 retains water, and may cover at least part of the surface of the specimen S. The water retention material 20 is paper (e.g., filter paper), a fabric, a nonwoven fabric, a sponge, a water-absorbing polymer, or the like.

The water retention material 20 may cover the entirety of the surface of the specimen S, or may cover part of the surface of the specimen S. In the example illustrated in FIGS. 1 and 2, the water retention material 20 covers the entirety of the upper surface of the specimen S (i.e., the surface of the specimen S is not exposed). It is desirable that the water retention material 20 cover the entirety of the exposed area of the specimen S in a state in which the specimen S is supported on the specimen support 10. This makes it possible to further reduce evaporation of water from the specimen S when evacuating the specimen chamber 2 (as described later).

The holder 30 is configured to be able to hold the water retention material 20. The holder 30 includes a water retention material holder 32 and a holder support member 34.

Figure 3:
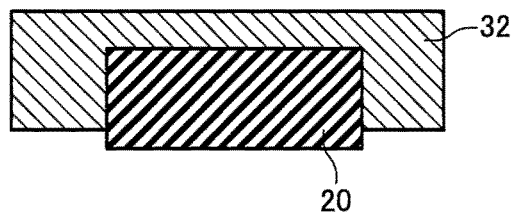
FIG. 3 is a cross-sectional view schematically illustrating a water retention material holder of a specimen stage according to the first embodiment.

The water retention material holder 32 is a holder that holds the water retention material 20. FIG. 3 is a cross-sectional view schematically illustrating the water retention material holder 32. As illustrated in FIG. 3, the water retention material holder 32 has a recess, and the water retention material 20 is fitted into the recess. Note that the water retention material holder 32 may hold the water retention material 20 in an arbitrary way. The way in which the water retention material holder 32 holds the water retention material 20 may be appropriately changed depending on the shape and the material of the water retention material 20.

The holder support member 34 supports the water retention material holder 32. For example, the holder support member 34 is an arm-like member that connects the water retention material holder 32 and the X moving mechanism 40X. The holder support member 34 is provided on the side of the specimen support 10 in the Y-axis direction, and is not provided on the side of the specimen support 10 in the X-axis direction. Therefore, the holder support member 34 does not hinder the movement of the specimen support 10 in the X-axis direction. As illustrated in FIG. 2, the specimen support 10 and the holder support member 34 are spaced in the Y-axis direction. Therefore, the holder support member 34 does not hinder the movement of the specimen support 10 in the Y-axis direction.

Since the holder support member 34 is connected to the X moving mechanism 40X that is immobilized, the water retention material holder 32 supported by the holder support member 34, and the water retention material 20 held by the water retention material holder 32 are immobilized. The holder support member 34 may be connected to the wall 3 or the bottom of the specimen chamber 2 (not illustrated in the drawings).

The X moving mechanism 40X is configured to be able to move the specimen support 10 in the X-axis direction. The X moving mechanism 40X moves the Y moving mechanism 40Y and the specimen support 10 (specimen S) placed on the X moving mechanism 40X in the X-axis direction. Since the water retention material 20 is held (immobilized) by the holder 30, the upper surface of the specimen S that is covered with the water retention material 20 can be exposed by moving the specimen support 10 using the X moving mechanism 40X (see FIG. 8).

Although an example in which the holder 30 is immobilized, and the upper surface of the specimen S is exposed by moving the specimen support 10 using the X moving mechanism 40X has been described above, the specimen support 10 may be immobilized, and the upper surface of the specimen S may be exposed by moving the holder 30 using a holder moving mechanism (see "1.3. Modification" described later). It is possible to expose the upper surface of the specimen S by thus moving the specimen support 10 and the holder 30 relative to each other.

The Y moving mechanism 40Y is configured to be able to move the specimen support 10 in the Y-axis direction. The Y moving mechanism 40Y moves the specimen support 10 (specimen S) placed on the Y moving mechanism 40Y in the Y-axis direction.

The Z moving mechanism 40Z is configured to be able to move the specimen support 10 in the Z-axis direction. The Z moving mechanism 40Z moves the X moving mechanism 40X, the Y moving mechanism 40Y, and the specimen support 10 (specimen S) in the Z-axis direction. Note that the Z moving mechanism 40Z may include a tilt mechanism that can tilt the specimen support 10.

The cooling section 50 cools the specimen support 10. The cooling section 50 may cool the specimen support 10 by circulating a cooled fluid through the specimen support 10, or may cool the specimen support 10 using a Peltier device or the like, for example. It is possible to cool the specimen S supported on the specimen support 10 by cooling the specimen support 10 using the cooling section 50.

1.2. Specimen Loading Method

Figure 4:
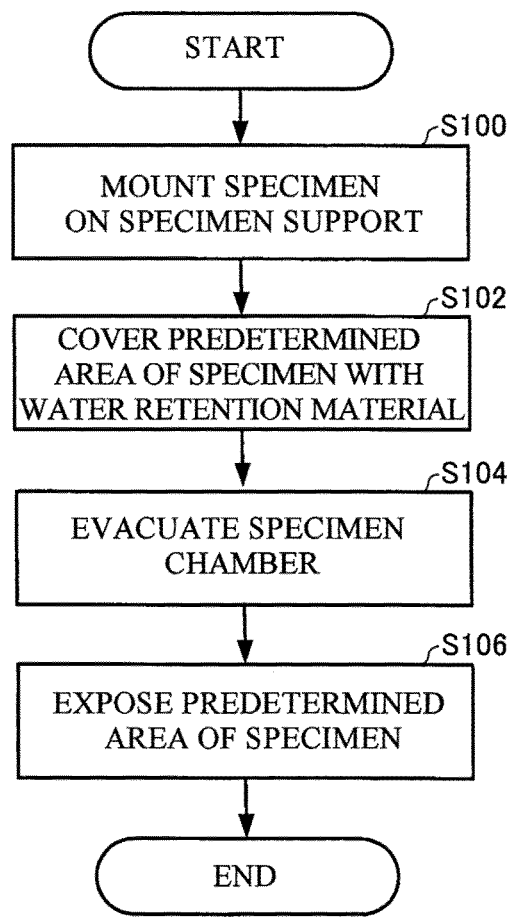
FIG. 4 is a flowchart illustrating an example of a specimen loading method that utilizes a specimen stage according to the first embodiment.

A specimen loading method that utilizes the specimen stage 100 according to the first embodiment is described below with reference to the drawings. FIG. 4 is a flowchart illustrating an example of the specimen loading method that utilizes the specimen stage 100 according to the first embodiment.

FIGS. 5 to 8 are schematic views illustrating a specimen loading step that utilizes the specimen stage 100. Note that FIGS. 5 to 8 illustrate a state in which the specimen stage 100 is placed in the specimen chamber 2 of the scanning electron microscope.

Figure 5:
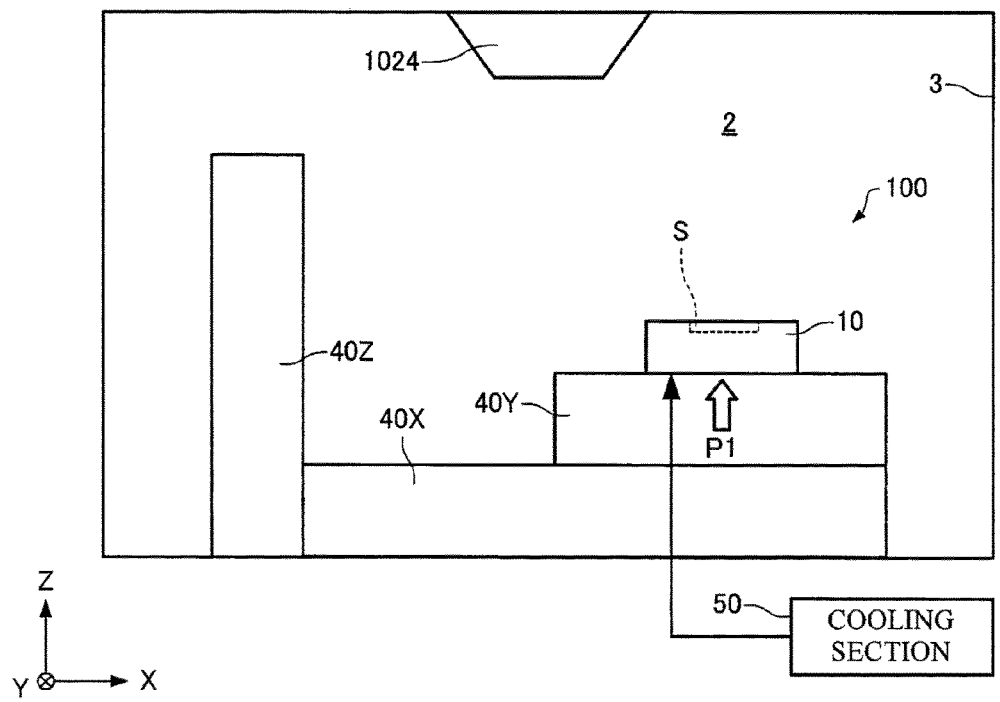
FIG. 5 is a schematic view illustrating a specimen loading step that utilizes a specimen stage according to the first embodiment.

As illustrated in FIG. 5, the specimen S is mounted on the specimen support 10 (step S100). The specimen S is thus supported on the specimen support 10 inside the specimen chamber 2. In this case, the specimen support 10 is situated at a first position P1. The first position P1 is a position at which an electron beam is not applied to the specimen S supported on the specimen support 10 inside the specimen chamber 2. For example, the first position P1 is a position at which the specimen S is not situated directly under the objective lens 1024. In the specimen loading step, the specimen chamber 2 is set to atmospheric pressure. The specimen support 10 is cooled to about 0° C. to about 1° C. using the cooling section 50. The specimen S supported on the specimen support 10 is thus cooled.

Figure 6:
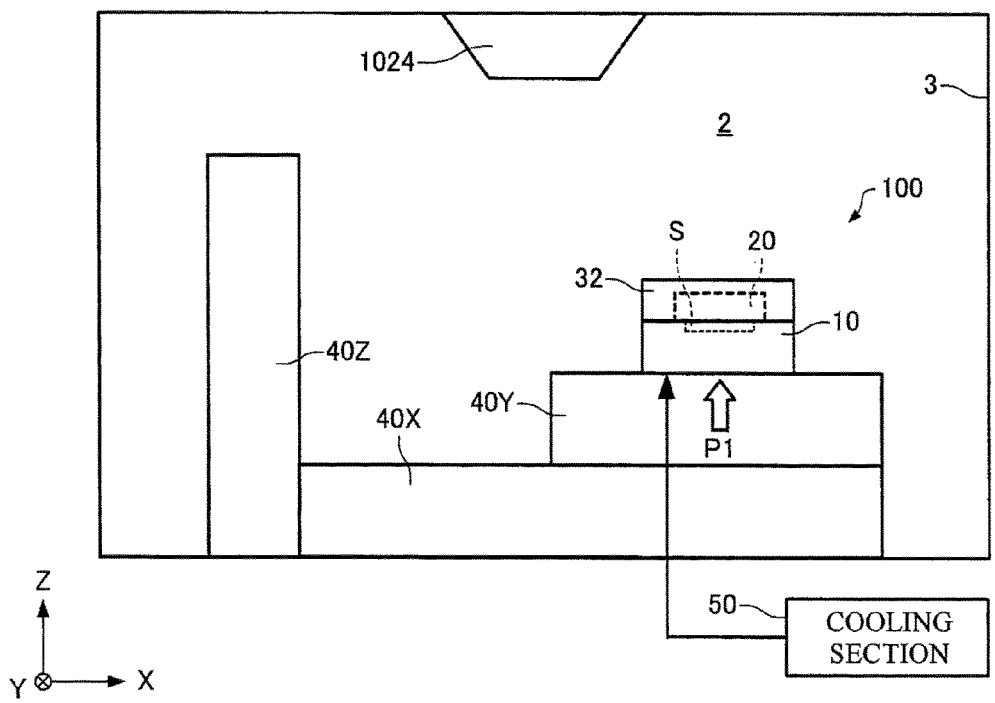
FIG. 6 is a schematic view illustrating a specimen loading step that utilizes a specimen stage according to the first embodiment.

As illustrated in FIG. 6, the upper surface (predetermined area) of the specimen S is covered with the water retention material 20 (step S102). In the step S102, the area of the specimen S (i.e., the upper surface of the specimen S) that is exposed in a state in which the specimen S is mounted on the specimen support 10 is covered with the water retention material 20. The water retention material 20 is placed on the upper surface of the specimen S in a state in which the water retention material 20 is fitted into the water retention material holder 32.

Although an example in which the upper surface of the specimen S is covered with the water retention material 20 after the specimen S has been mounted on the specimen support 10 has been described above, the specimen S of which the upper surface has first been covered with the water retention material 20, may be mounted on the specimen support 10.

Figure 7:
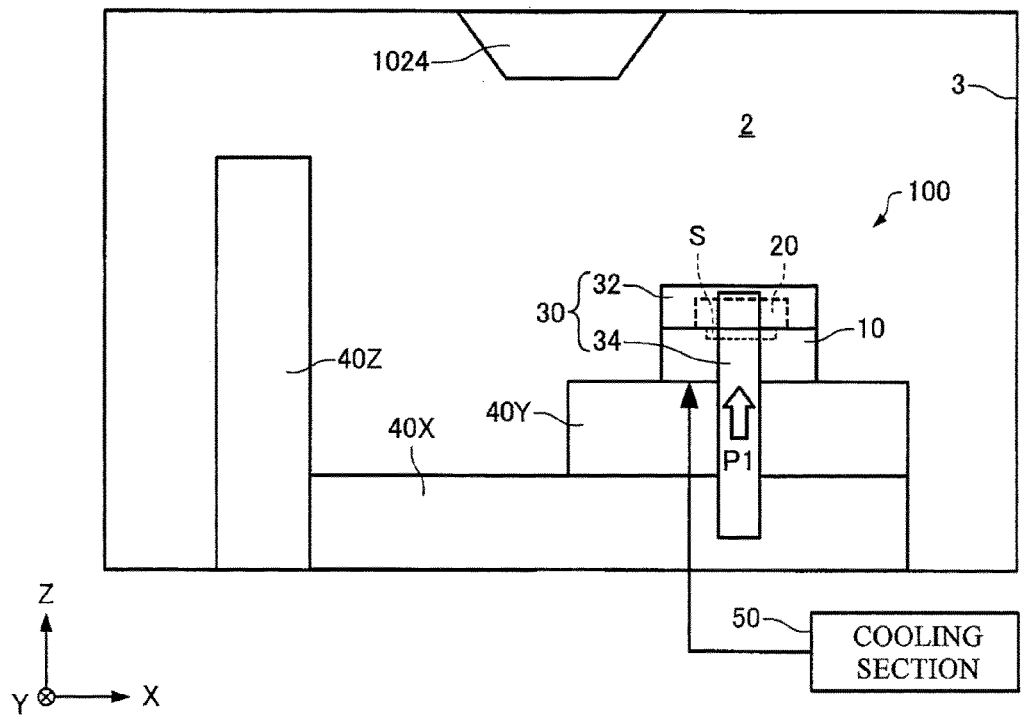
FIG. 7 is a schematic view illustrating a specimen loading step that utilizes a specimen stage according to the first embodiment.

As illustrated in FIG. 7, the water retention material 20 is immobilized. The water retention material 20 is immobilized by immobilizing the water retention material holder 32 using the holder support member 34. Therefore, the water retention material 20 does not move even if the specimen support 10 (specimen S) is moved.

The specimen chamber 2 is then evacuated (step S104). The specimen chamber 2 is evacuated using the evacuation device that is connected to the specimen chamber 2. The evacuation device evacuates the specimen chamber 2 so that the pressure inside the specimen chamber 2 is stably maintained at about 650 Pa.

The step S104 that evacuates the specimen chamber 2 is performed in a state in which the upper surface of the specimen S is covered with the water retention material 20. This makes it possible to reduce evaporation of water from the specimen S. Therefore, it is possible to prevent a situation in which the specimen S dries. It is also possible to prevent a situation in which the specimen S freezes due to heat of evaporation. The specimen S has been cooled to 0° C. to 1° C. Therefore, it is possible to keep the water contained in the specimen S in a liquid phase even when the pressure inside the specimen chamber 2 has reached 650 Pa.

Figure 8:
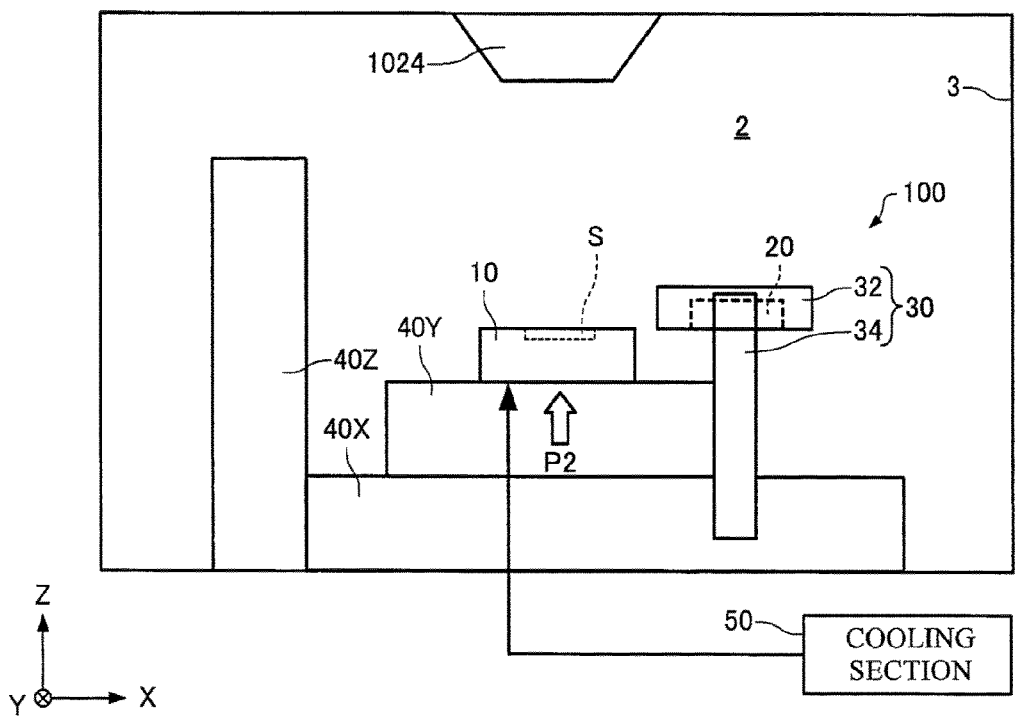
FIG. 8 is a schematic view illustrating a specimen loading step that utilizes a specimen stage according to the first embodiment.

As illustrated in FIG. 8, the upper surface (predetermined area) of the specimen S that is covered with the water retention material 20 is exposed (step S106). In the step S106, the upper surface of the specimen S is exposed by moving the specimen S and the water retention material 20 relative to each other. More specifically, the upper surface of the specimen S is exposed by moving the specimen support 10 from the first position P1 to a second position P2 using the X moving mechanism 40X in a state in which the water retention material 20 is immobilized using the holder 30. The second position P2 is a position (observation position or analysis position) at which an electron beam is applied to the upper surface of the specimen S that is supported on the specimen support 10. In the example illustrated in FIG. 8, the second position P2 is a position at which the specimen S is situated directly under the objective lens 1024.

Although FIG. 8 illustrates an example in which the entirety of the upper surface of the specimen S is exposed by moving the specimen support 10, only part of the upper surface of the specimen S may be exposed.

The specimen S can thus be loaded into the specimen chamber 2.

After the specimen S has been loaded into the specimen chamber 2 (i.e., after the upper surface of the specimen S has been exposed), an electron beam is applied to the upper surface of the specimen S. It is possible to implement SEM observation or elemental analysis by detecting secondary electrons or characteristic X-rays generated (emitted or released) from the specimen S. Since the area of the specimen S to which an electron beam is applied (i.e., the upper surface of the specimen S) can be covered the with water retention material 20 until just before an electron beam is applied to the specimen S, it is possible to observe or analyze the specimen S in a state in which the specimen S contains water while preventing a situation in which the specimen S dries or freezes.

The specimen stage 100 has the following features, for example.

The specimen stage 100 includes the specimen support 10 that supports the specimen S, the holder 30 that can hold the water retention material 20 that covers a predetermined area (upper surface) of the specimen S that is supported on the specimen support 10, and the X moving mechanism 40X that moves the specimen support 10. The specimen stage 100 is configured so that the predetermined area of the specimen S that has been covered with the water retention material 20 can be exposed by moving the specimen support 10 using the X moving mechanism 40X. Therefore, the specimen stage 100 can reduce evaporation of water from the specimen S, and prevent a situation in which the specimen S dries or freezes when the specimen S is loaded into the specimen chamber 2 by covering the predetermined area of the specimen S with the water retention material 20, and can expose the predetermined area of the specimen S when the specimen S is observed or analyzed.

Since the specimen stage 100 includes the cooling section 50 that cools the specimen support 10, it is possible to keep the water contained in the specimen S in a liquid phase (as compared with the case where the specimen S is not cooled) even when the pressure inside the specimen chamber 2 has been reduced, for example. When the pressure inside the specimen chamber 2 is set to 650 Pa, for example, it is possible to keep the water contained in the specimen S in a liquid phase by setting the temperature of the specimen S to about 0° C. to about 1° C.

The specimen loading method that utilizes the specimen stage 100 includes a step that mounts the specimen S on the specimen support 10 (step S100), a step that covers a predetermined area (upper surface) of the specimen S with the water retention material 20 (step S102), a step that evacuates the specimen chamber 2 in which the specimen S is placed, the predetermined area of the specimen S being covered with the water retention material 20 (step S106), and a step that exposes the predetermined area of the specimen S that is covered with the water retention material 20 (step S108). According to the specimen loading method, since the step that evacuates the specimen chamber 2 is performed in a state in which the predetermined area of the specimen S is covered with the water retention material 20, it is possible to reduce evaporation of water from the specimen S. Therefore, the specimen loading method can prevent a situation in which the specimen S dries when loading the specimen S into the specimen chamber 2. The specimen loading method can also prevent a situation in which the specimen S freezes due to heat of evaporation.

According to the specimen loading method that utilizes the specimen stage 100, the predetermined area of the specimen S is exposed in the step that exposes the predetermined area of the specimen S by moving the specimen S and the water retention material 20 relative to each other. Therefore, it is possible to easily expose the predetermined area of the specimen S as compared with the case of removing the water retention material 20 from the specimen S using a manipulator or the like, for example.

1.3. Modification

Figure 9:
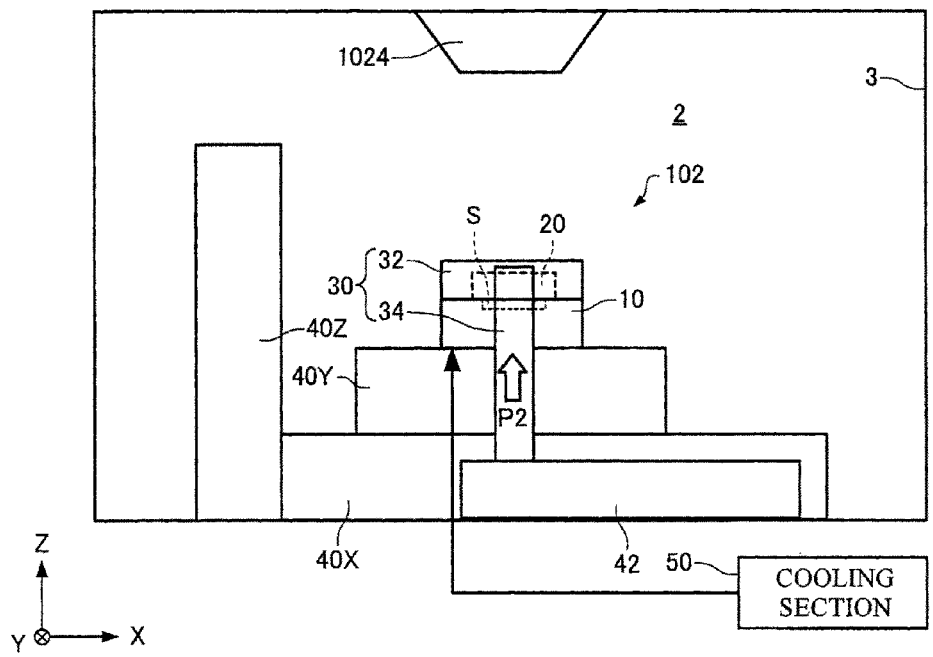
FIG. 9 is a schematic view illustrating the configuration of a specimen stage according to a modification of the first embodiment.
Figure 10:
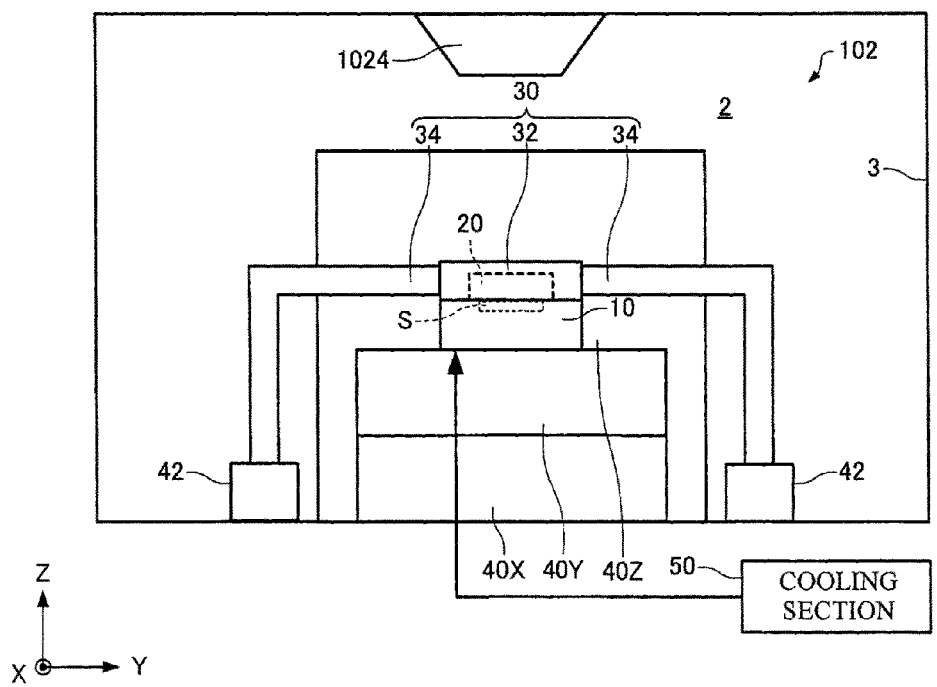
FIG. 10 is a schematic view illustrating the configuration of a specimen stage according to a modification of the first embodiment.

A specimen stage according to a modification of the first embodiment is described below with reference to the drawings. FIGS. 9 and 10 are schematic views illustrating the configuration of a specimen stage 102 according to the modification of the first embodiment. Note that the members of the specimen stage 102 according to the modification of the first embodiment that have the same functions as those of the specimen stage 100 according to the first embodiment are indicated by the same reference signs (symbols), and detailed description thereof is omitted.

The specimen stage 100 is configured so that the upper surface of the specimen S that is covered with the water retention material 20 is exposed by moving the specimen support 10 using the X moving mechanism 40X (see FIGS. 7 and 8).

The specimen stage 102 is configured so that the upper surface of the specimen S that is covered with the water retention material 20 is exposed by moving the holder 30 using a holder moving mechanism 42.

As illustrated in FIGS. 9 and 10, the specimen stage 102 includes the holder moving mechanism 42. The holder moving mechanism 42 is configured to be able to move the holder 30 in the X-axis direction. The holder moving mechanism 42 is connected to the holder support member 34. The water retention material holder 32 and the water retention material 20 that is held by the water retention material holder 32 are moved by moving the holder support member 34. Since the specimen S is secured on the specimen support 10, the upper surface of the specimen S that is covered with the water retention material 20 can be exposed by moving the holder 30 using the holder moving mechanism 42 so as to move the water retention material 20 (see FIG. 11).

Figure 11:
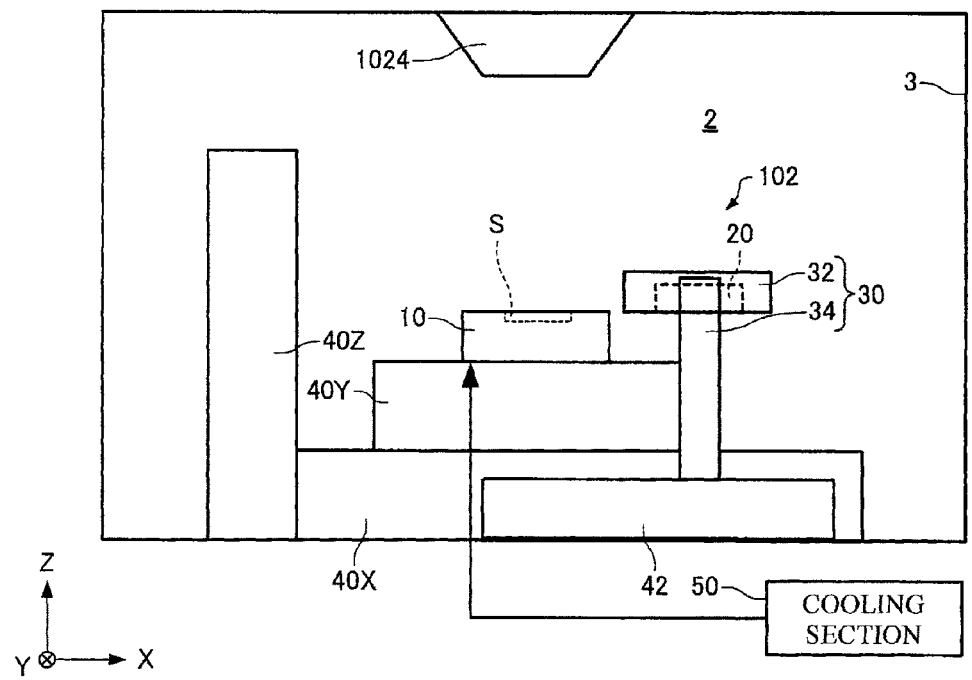
FIG. 11 is a schematic view illustrating a specimen loading step that utilizes a specimen stage according to a modification of the first embodiment.

A specimen loading method that utilizes the specimen stage 102 according to the modification is described below with reference to the drawings. FIG. 11 is a schematic view illustrating a step that exposes a predetermined area (upper surface) of the specimen S that is covered with the water retention material 20 (step S106 illustrated in FIG. 4). The specimen loading method is described below with reference to FIG. 4 (flowchart). Note that the following description focuses on the differences between the specimen loading method that utilizes the specimen stage 102 according to the modification and the specimen loading method that utilizes the specimen stage 100 according to the first embodiment, and description of the same features is omitted.

As illustrated in FIG. 9, the specimen S is mounted on the specimen support 10 (step S100). In this case, the specimen support 10 is situated at the second position P2.

A predetermined area (upper surface) of the specimen S is covered with the water retention material 20 (step S102). The water retention material 20 is placed on the specimen S in a state in which the water retention material 20 is fitted into the water retention material holder 32.

The water retention material 20 is then held using the holder 30. The water retention material 20 is held using the holder 30 by attaching the holder support member 34 to the water retention material holder 32 and the holder moving mechanism 42. The water retention material 20 can thus be moved using the holder moving mechanism 42.

The specimen chamber 2 is then evacuated (step S104). The specimen chamber 2 is evacuated using the evacuation device so that the pressure inside the specimen chamber 2 is stably maintained at about 650 Pa.

The step S104 that evacuates the specimen chamber 2 is performed in a state in which the upper surface of the specimen S is covered with the water retention material 20. This makes it possible to reduce evaporation of water from the specimen S. Therefore, it is possible to prevent a situation in which the specimen S dries. It is also possible to prevent a situation in which the specimen S freezes due to heat of evaporation. The specimen S has been cooled to 0° C. to 1° C. Therefore, it is possible to keep the water contained in the specimen S in a liquid phase even when the pressure inside the specimen chamber 2 has reached 650 Pa.

As illustrated in FIG. 11, the predetermined area (upper surface) of the specimen S that is covered with the water retention material 20 is exposed (step S106). In the step S106, the upper surface of the specimen S is exposed by moving the specimen S and the water retention material 20 relative to each other. More specifically, the upper surface of the specimen S is exposed by moving the water retention material 20 using the holder moving mechanism 42 in a state in which the specimen S is immobilized using the specimen support 10.

The specimen S can thus be loaded into the specimen chamber 2.

The specimen stage 102 and the specimen loading method that utilizes the specimen stage 102 can achieve the same advantageous effects as those achieved by the specimen stage 100 and the specimen loading method that utilizes the specimen stage 100.

2. Second Embodiment 2.1. Specimen Stage

Figure 12:
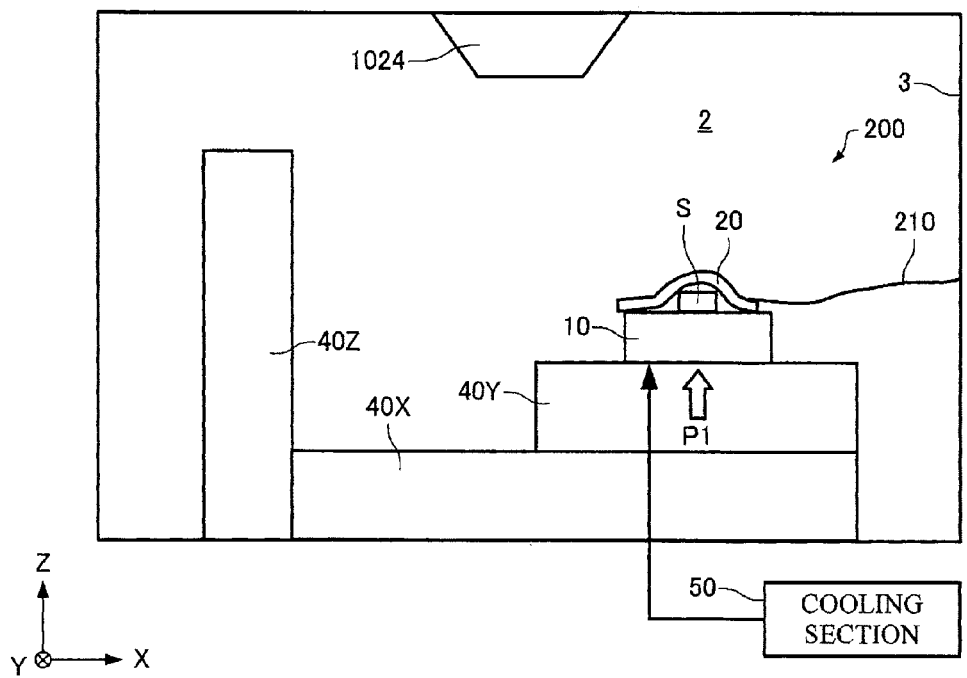
FIG. 12 is a schematic view illustrating the configuration of a specimen stage according to the second embodiment.

A specimen stage according to a second embodiment of the invention is described below with reference to the drawings. FIG. 12 is a schematic view illustrating the configuration of a specimen stage 200 according to the second embodiment. Note that FIG. 12 illustrates a state in which the specimen stage 200 is placed in a specimen chamber 2 of a scanning electron microscope. The members of the specimen stage 200 according to the second embodiment that have the same functions as those of the specimen stage 100 according to the first embodiment are indicated by the same reference signs (symbols), and detailed description thereof is omitted.

As illustrated in FIG. 12, the specimen stage 200 includes a specimen support 10, a water retention material 20, an X moving mechanism 40X, a Y moving mechanism 40Y, a Z moving mechanism 40Z, and a restriction section 210.

The water retention material 20 is in the shape of a sheet. For example, the water retention material 20 is filter paper. Water can be retained by allowing the filter paper to absorb water. In the example illustrated in FIG. 12, the water retention material 20 covers the upper surface and the side surface of the specimen S. Since the water retention material 20 is in the shape of a sheet, it is possible to easily cover the specimen S with the water retention material 20.

The restriction section 210 is a member that restricts the movement of the water retention material 20 (that covers a predetermined area (upper surface and side surface) of the specimen S that is supported on the specimen support 10) along with the movement of the specimen support 10. In the example illustrated in FIG. 12, the restriction section 210 is a thread-like member that connects the wall 3 of the specimen chamber 2 and the water retention material 20. The restriction section 210 is provided so that one end of the restriction section 210 is connected to the wall 3, and the other end of the restriction section 210 is connected to the water retention material 20. The restriction section 210 is a thread, a wire, or the like, for example.

The restriction section (thread) 210 is provided so that the thread is tense when the specimen support 10 illustrated in FIG. 12 is situated at the first position P1. Therefore, when the specimen support 10 is moved to the second position P2, the water retention material 20 is pulled by the restriction section 210 (i.e., the movement of the water retention material 20 is restricted), and the upper surface and the side surface of the specimen S that have been covered with the water retention material 20 are exposed.

2.2. Specimen Loading Method

Figure 13:
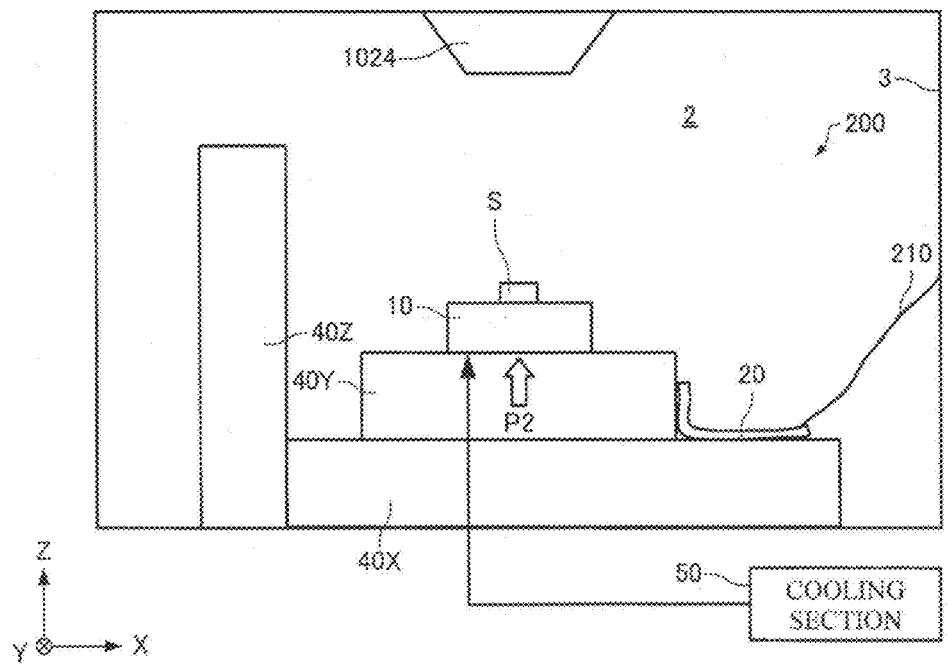
FIG. 13 is a schematic view illustrating a specimen loading step that utilizes a specimen stage according to the second embodiment.

A specimen loading method that utilizes the specimen stage 200 according to the second embodiment is described below with reference to the drawings. FIG. 13 is a schematic view illustrating a step that exposes a predetermined area (upper surface and side surface) of the specimen S that is covered with the water retention material 20 (step S106 illustrated in FIG. 4). The specimen loading method is described below with reference to FIG. 4 (flowchart). Note that the following description focuses on the differences between the specimen loading method that utilizes the specimen stage 200 according to the second embodiment and the specimen loading method that utilizes the specimen stage 100 according to the first embodiment, and description of the same features is omitted.

As illustrated in FIG. 12, the specimen S is mounted on the specimen support 10 (step S100). In this case, the specimen support 10 is situated at the first position P1. A predetermined area (upper surface and side surface) of the specimen S is covered with the water retention material 20 (step S102). More specifically, the water retention material 20 that is in the shape of a sheet is put on the specimen S.

The restriction section 210 is then secured on the water retention material 20. More specifically, one end of the restriction section 210 is connected to (secured on) the wall 3 of the specimen chamber 2, and the other end of the restriction section 210 is connected to (secured on) the water retention material 20. Note that one end of the restriction section 210 may be sewn on the water retention material 20 in advance, and the other end of the restriction section 210 may be connected to (secured on) the wall 3 of the specimen chamber 2 after covering the specimen S with the water retention material 20.

The specimen chamber 2 is then evacuated (step S104). The specimen chamber 2 is evacuated using the evacuation device so that the pressure inside the specimen chamber 2 is stably maintained at about 650 Pa.

The step S104 that evacuates the specimen chamber 2 is performed in a state in which the upper surface and the side surface of the specimen S are covered with the water retention material 20. This makes it possible to reduce evaporation of water from the specimen S. Therefore, it is possible to prevent a situation in which the specimen S dries. It is also possible to prevent a situation in which the specimen S freezes due to heat of evaporation. The specimen S has been cooled to 0° C. to 1° C. Therefore, it is possible to keep the water contained in the specimen S in a liquid phase even when the pressure inside the specimen chamber 2 has reached 650 Pa.

As illustrated in FIG. 13, the predetermined area (upper surface and side surface) of the specimen S that is covered with the water retention material 20 is exposed (step S108). In the step S108, the upper surface and the side surface of the specimen S are exposed by moving the specimen S and the water retention material 20 relative to each other. More specifically, the specimen support 10 is moved from the first position P1 to the second position P2 using the X moving mechanism 40X. In this case, since the movement of the water retention material 20 is restricted by the restriction section 210 (i.e., the water retention material 20 is pulled by the restriction section 210), the water retention material 20 is removed from the specimen S so that the upper surface and the side surface of the specimen S that have been covered with the water retention material 20 are exposed.

The specimen S can thus be loaded into the specimen chamber 2.

Since the specimen stage 200 is configured so that the movement of the water retention material 20 (that covers the predetermined area (upper surface and side surface) of the specimen S) along with the movement of the specimen support 10 can be restricted by the restriction section 210, the predetermined area of the specimen S that has been covered with the water retention material 20 can be exposed as described above. Therefore, the specimen stage 200 can reduce evaporation of water from the specimen S, and prevent a situation in which the specimen S dries or freezes when the specimen S is loaded into the specimen chamber 2 by covering the predetermined area of the specimen S with the water retention material 20, and can expose the predetermined area of the specimen S when the specimen S is observed or analyzed.

Figure 14:
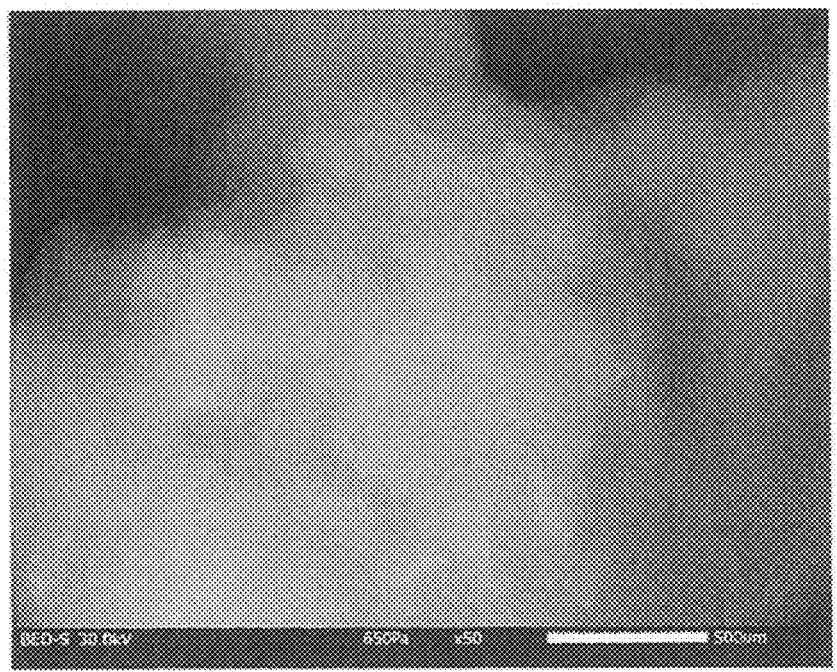
FIG. 14 illustrates an SEM photograph obtained by observing a water-absorbing polymer using an SEM.
Figure 15:
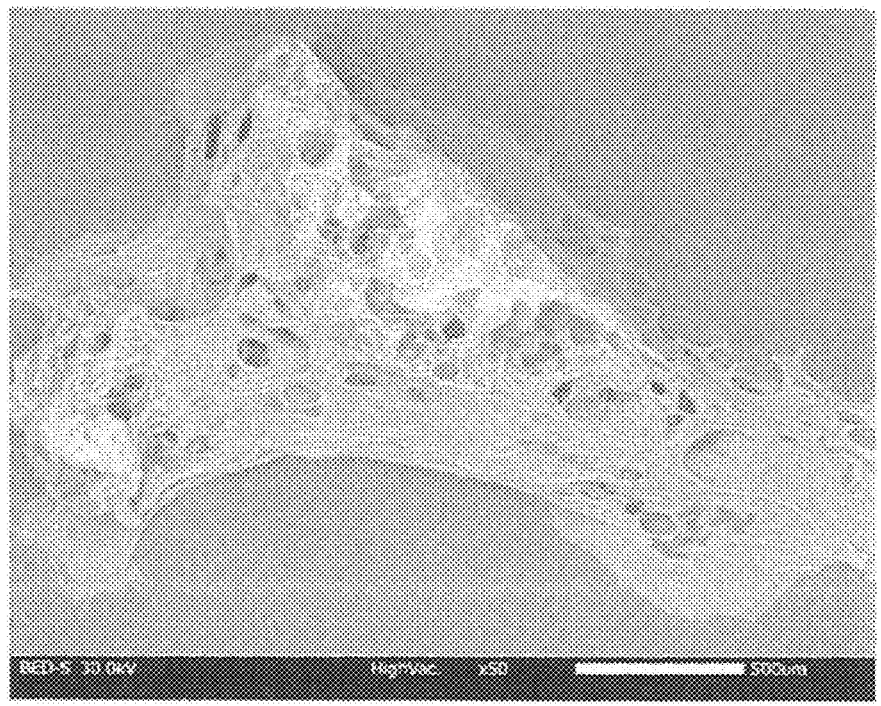
FIG. 15 illustrates an SEM photograph obtained by observing a water-absorbing polymer using an SEM.
Figure 16:
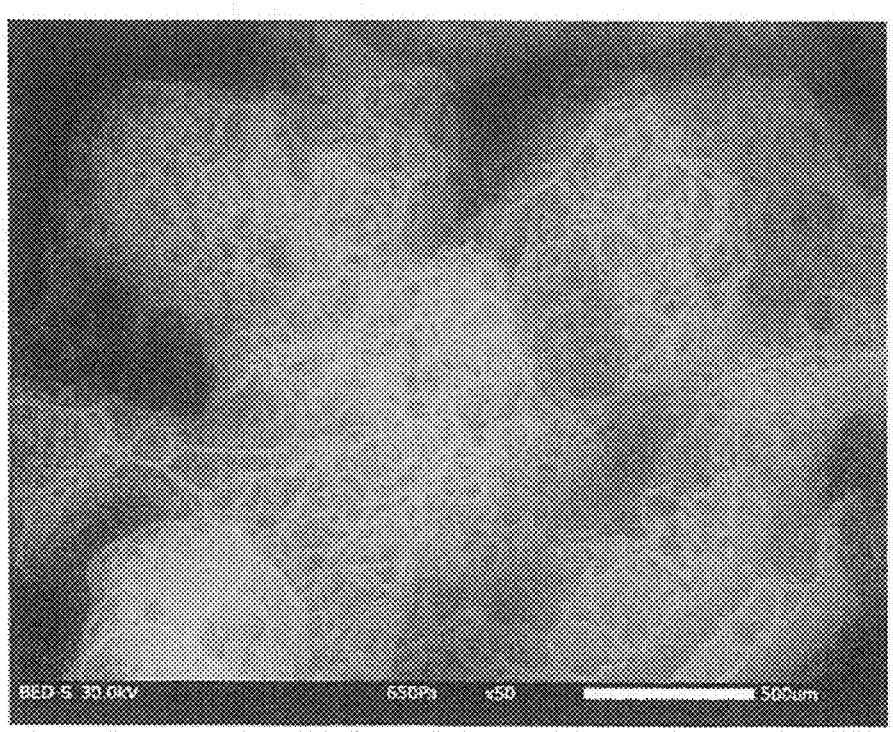
FIG. 16 illustrates an SEM photograph obtained by observing a water-absorbing polymer using an SEM.

FIGS. 14 to 16 illustrate SEM photographs obtained by observing a water-absorbing polymer (that contained water and expanded) using an SEM.

The SEM photograph illustrated in FIG. 14 was obtained by mounting the water-absorbing polymer (that contained water and expanded) on a cooled specimen stage (0° C.), covering the water-absorbing polymer with filter paper that had absorbed water, evacuating the specimen chamber so that the degree of vacuum inside the specimen chamber was 650 Pa, removing the filter paper to expose the surface of the water-absorbing polymer, and observing the water-absorbing polymer using an SEM.

The SEM photograph illustrated in FIG. 15 was obtained by mounting the water-absorbing polymer (that contained water and expanded) on a specimen stage, evacuating the specimen chamber so that the degree of vacuum inside the specimen chamber was 650 Pa, and observing the water-absorbing polymer using an SEM.

The SEM photograph illustrated in FIG. 16 was obtained by mounting the water-absorbing polymer (that contained water and expanded) on a cooled specimen stage (0° C.), evacuating the specimen chamber so that the degree of vacuum inside the specimen chamber was 650 Pa, and observing the water-absorbing polymer using an SEM.

It was observed from the SEM photograph illustrated in FIG. 15 that the water was completely removed from the water-absorbing polymer (i.e., the water-absorbing polymer was dried).

It was observed from the SEM photograph illustrated in FIG. 16 that the water was not completely removed from the water-absorbing polymer, but the surface of the water-absorbing polymer dried and froze.

It was observed from the SEM photograph illustrated in FIG. 14 that the water remained on the surface of the water-absorbing polymer in a liquid phase. It was confirmed from the SEM photograph illustrated in FIG. 14 that the water contained in the water-absorbing polymer did not freeze.

3. Third Embodiment 3.1. Specimen Stage

Figure 17:
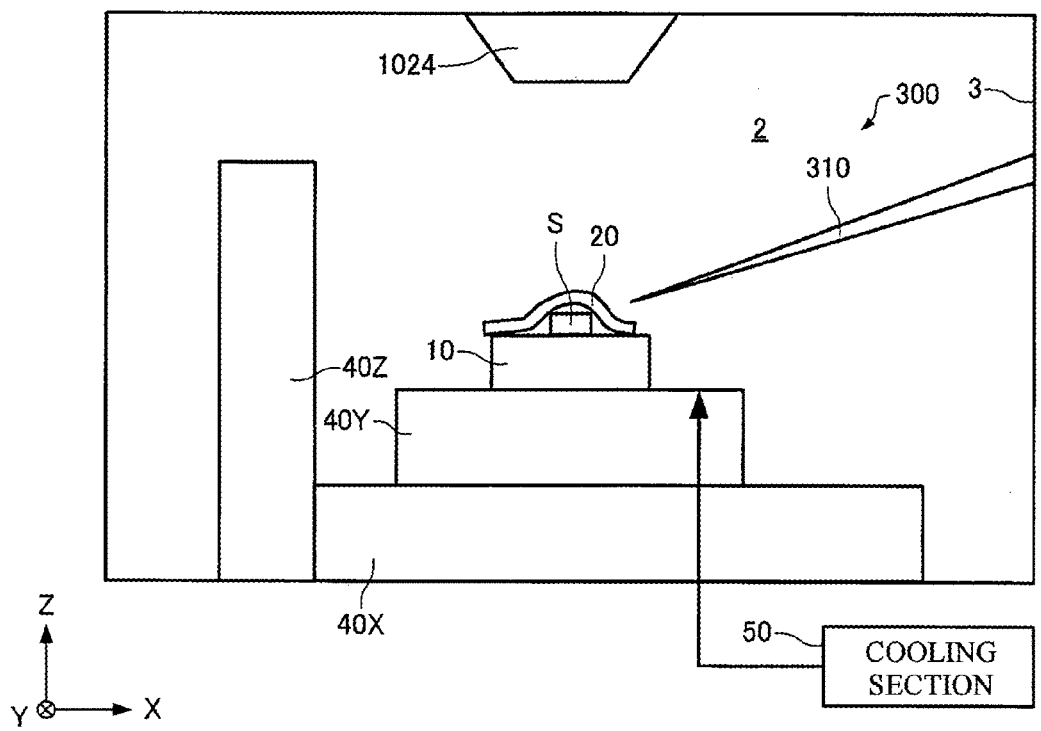
FIG. 17 is a schematic view illustrating the configuration of a specimen stage according to the third embodiment.

A specimen stage according to a third embodiment of the invention is described below with reference to the drawings. FIG. 17 is a schematic view illustrating the configuration of a specimen stage 300 according to the third embodiment. Note that FIG. 17 illustrates a state in which the specimen stage 300 is placed in a specimen chamber 2 of a scanning electron microscope. The members of the specimen stage 300 according to the third embodiment that have the same functions as those of the specimen stage 100 according to the first embodiment are indicated by the same reference signs (symbols), and detailed description thereof is omitted.

As illustrated in FIG. 17, the specimen stage 300 includes a specimen support 10, a water retention material 20, an X moving mechanism 40X, a Y moving mechanism 40Y, a Z moving mechanism 40Z, and a manipulator 310.

The manipulator 310 is placed in the specimen chamber 2. The manipulator 310 can be operated externally. The water retention material 20 can be moved using the manipulator 310.

3.2. Specimen Loading Method

Figure 18:
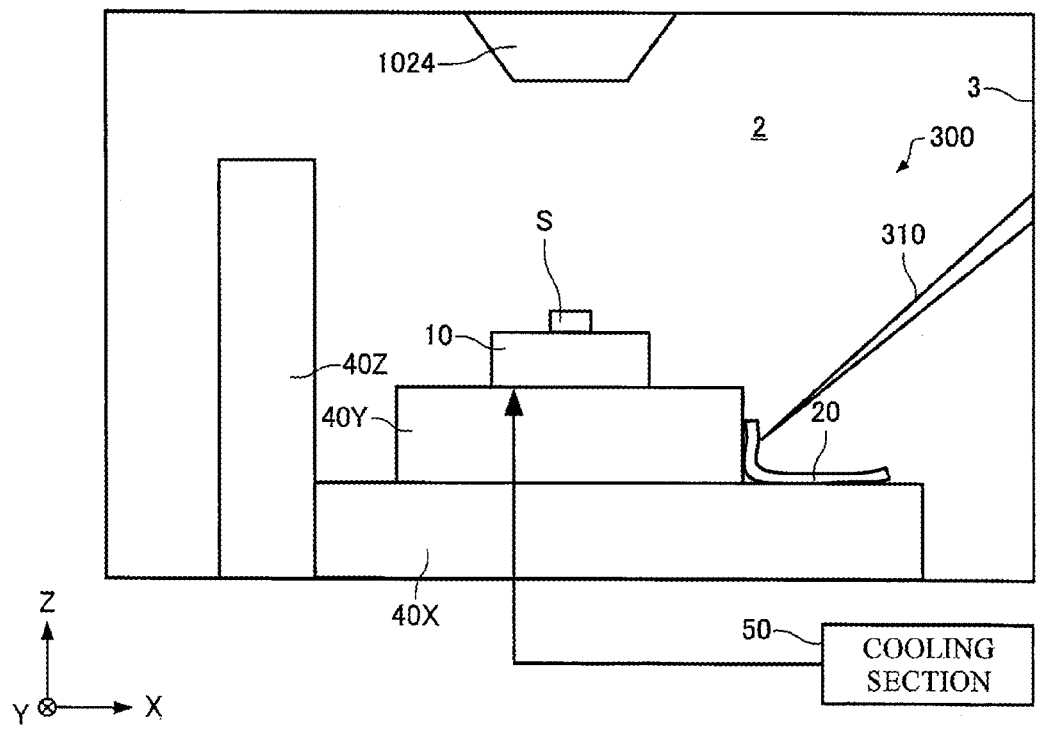
FIG. 18 is a schematic view illustrating a specimen loading step that utilizes a specimen stage according to the third embodiment.

A specimen loading method that utilizes the specimen stage 300 according to the third embodiment is described below with reference to the drawings. FIG. 18 is a schematic view illustrating a step that exposes a predetermined area (upper surface and side surface) of the specimen S that is covered with the water retention material 20 (step S106 illustrated in FIG. 4). The specimen loading method is described below with reference to FIG. 4 (flowchart). Note that the following description focuses on the differences between the specimen loading method that utilizes the specimen stage 300 according to the third embodiment and the specimen loading method that utilizes the specimen stage 100 according to the first embodiment, and description of the same features is omitted.

As illustrated in FIG. 17, the specimen S is mounted on the specimen support 10 (step S100).

A predetermined area (upper surface and side surface) of the specimen S is covered with the water retention material 20 (step S102). In the step S102, the water retention material 20 that is in the shape of a sheet is put on the specimen S.

The specimen chamber 2 is then evacuated (step S104). The specimen chamber 2 is evacuated using the evacuation device so that the pressure inside the specimen chamber 2 is stably maintained at about 650 Pa.

The step S104 that evacuates the specimen chamber 2 is performed in a state in which the upper surface and the side surface of the specimen S are covered with the water retention material 20. This makes it possible to reduce evaporation of water from the specimen S. Therefore, it is possible to prevent a situation in which the specimen S dries. It is also possible to prevent a situation in which the specimen S freezes due to heat of evaporation. The specimen S has been cooled to 0° C. to 1° C. Therefore, it is possible to keep the water contained in the specimen S in a liquid phase even when the pressure inside the specimen chamber 2 has reached 650 Pa.

As illustrated in FIG. 18, the predetermined area (upper surface and side surface) of the specimen S that is covered with the water retention material 20 is exposed (step S108). In the step S108, the upper surface and the side surface of the specimen S are exposed by removing the water retention material 20 from the specimen S using the manipulator 310.

The specimen S can thus be loaded into the specimen chamber 2.

The specimen loading method that utilizes the specimen stage 300 according to the third embodiment can achieve the same advantageous effects as those achieved by the specimen loading method that utilizes the specimen stage 100 according to the first embodiment.

4. Fourth Embodiment

Figure 19:
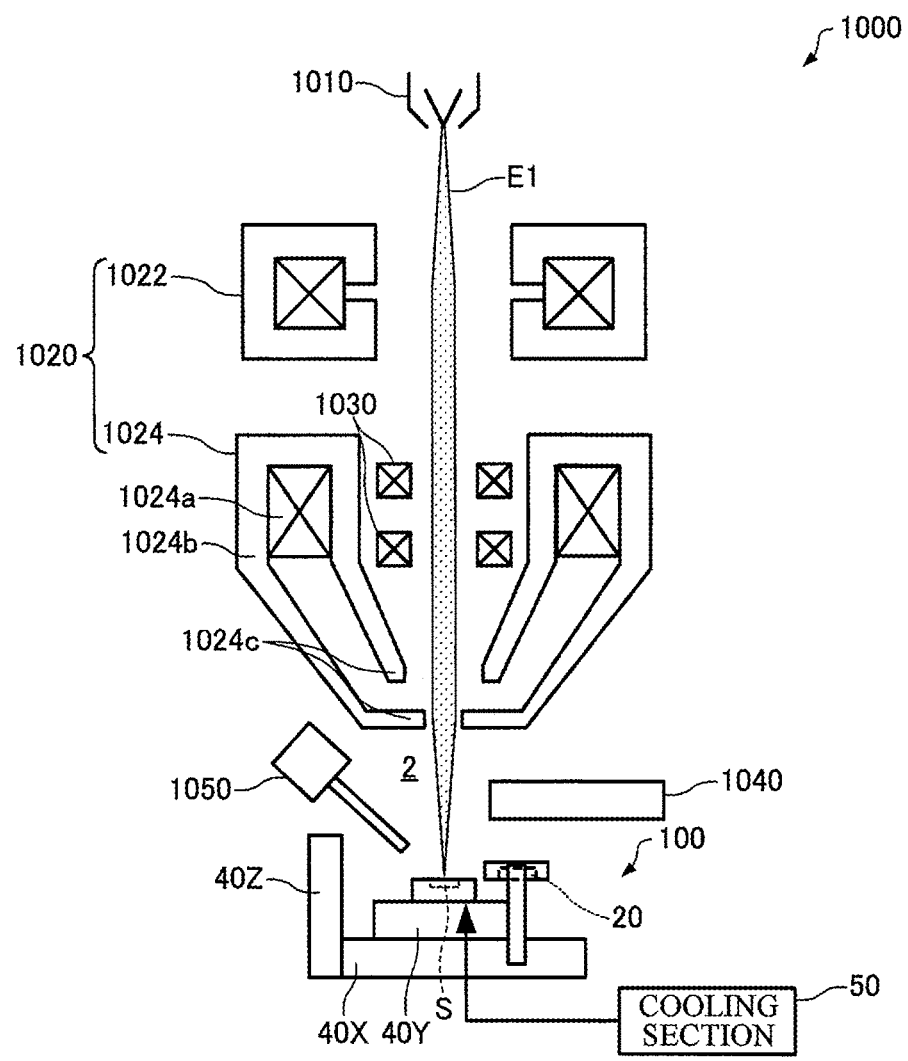
FIG. 19 is a schematic view illustrating the configuration of a charged particle beam device according to the fourth embodiment.

A charged particle beam device according to a fourth embodiment of the invention is described below with reference to the drawings. FIG. 19 is a schematic view illustrating the configuration of a charged particle beam device 1000 according to the fourth embodiment.

The charged particle beam device 1000 includes the specimen stage according to the invention. An example in which the specimen stage 100 described above is used as the specimen stage according to the invention is described below.

As illustrated in FIG. 19, the charged particle beam device 1000 includes an electron beam source 1010, an optical system 1020, a scanning deflector 1030, the specimen stage 100, a secondary electron detector 1040, and a radiation detector 1050. Note that the wall 3 of the specimen chamber 2 is omitted in FIG. 19.

The charged particle beam device 1000 is a device that is configured so that an electron beam E1 generated by the electron beam source 1010 is focused by the optical system 1020, and used as an electron probe, and secondary electrons emitted from the electron probe irradiation point when the surface of the specimen S is scanned with the electron probe are detected by the secondary electron detector 1040 to generate an image. The charged particle beam device 1000 is configured so that characteristic X-rays generated when the electron beam E1 is applied to the specimen S are detected by the radiation detector 1050 (energy-dispersive radiation detector), and energy-discriminated to obtain a spectrum. Specifically, the charged particle beam device 1000 is a scanning electron microscope that includes an energy-dispersive X-ray detector.

The charged particle beam device 1000 is a device that makes it possible to implement observation and analysis in a state in which the degree of vacuum inside the specimen chamber 2 is set to about several tens of Pa to about several hundred Pa. Specifically, the charged particle beam device 1000 is a low-vacuum SEM.

The electron beam source 1010 generates the electron beam (charged particle beam) E1. The electron beam source 1010 is a known electron gun, for example. The electron beam source 1010 accelerates electrons released (emitted) from a cathode using an anode to emit the electron beam E1. The electron gun that may be used as the electron beam source 1010 is not particularly limited. For example, a thermionic-emission electron gun, a thermal field-emission electron gun, a cold cathode field-emission electron gun, and the like may be used as the electron beam source 1010.

The optical system 1020 applies the electron beam E1 generated by the electron beam source 1010 to the specimen S. The optical system 1020 includes a condenser lens 1022 and an objective lens 1024.

The condenser lens 1022 is disposed in the subsequent stage with respect to the electron beam source 1010 (i.e., on the downstream side with respect to the electron beam source 1010 that emits the electron beam E1). The condenser lens 1022 is a lens for focusing the electron beam E1.

The objective lens 1024 is disposed in the subsequent stage with respect to the condenser lens 1022. The objective lens 1024 is a final-stage electron probe-forming lens that is disposed in the preceding stage with respect to the specimen S. The objective lens 1024 includes a coil 1024a, a yoke 1024b, and a pole piece 1024c. The objective lens 1024 is configured so that lines of magnetic force generated by the coil 1024a are confined in the yoke 1024b that is formed of a material (e.g., iron) that exhibits high permeability, and the lines of magnetic force that are distributed at high density leak toward the optical axis through a gap (lens gap) formed in the yoke 1024b. The gap is formed by the pole piece 1024c. In the example illustrated in FIG. 19, the specimen S is disposed outside the pole piece 1024c.

The scanning deflector (scanning coil) 1030 is disposed between the condenser lens 1022 and the objective lens 1024. The scanning deflector 1030 is an electromagnetic coil that scans the specimen S with the electron beam E1 that has been focused by the condenser lens 1022 and the objective lens 1024, for example. The scanning deflector 1030 scans the specimen S with the electron beam E1 by deflecting the electron beam E1. The scanning deflector 1030 scans the specimen S with the electron beam E1 based on a scan signal output from a scan signal generation section (not illustrated in the drawings).

The specimen stage 100 can support the specimen S, and move the specimen S. The specimen stage 100 is configured so that the specimen S can be moved in the horizontal direction using the X moving mechanism 40X and the Y moving mechanism 40Y, and can be moved in the vertical direction using the Z moving mechanism 40Z. The specimen stage 100 can reduce evaporation of water from the specimen S, and prevent a situation in which the specimen S dries or freezes when the specimen S is loaded into the specimen chamber 2 by covering the predetermined area of the specimen S with the water retention material 20, and can expose the predetermined area of the specimen S when the specimen S is observed or analyzed.

The secondary electron detector 1040 detects secondary electrons released (emitted) from the specimen S when the electron beam E1 has been applied to the specimen S. The secondary electron detector 1040 includes a scintillator and a photomultiplier, for example. A secondary electron detection signal (intensity signal) detected by the secondary electron detector 1040 is stored in a storage section (not illustrated in the drawings) as image data that is synchronized with the scan signal that is used in connection with the electron beam E1. A scanning electron image (SEM image) of the specimen S is generated based on the image data.

The radiation detector 1050 detects characteristic X-rays (radiation) generated (emitted) from the specimen S when the electron beam E1 has been applied to the specimen S. The radiation detector 1050 is an energy-dispersive X-ray detector. The radiation detector 1050 includes a silicon-drift detector (SDD), for example.

Since the charged particle beam device 1000 includes the specimen stage 100, the charged particle beam device 1000 can prevent a situation in which the specimen S dries and freezes when the specimen S is loaded into the specimen chamber 2. Therefore, the charged particle beam device 1000 makes it possible to observe or analyze the specimen S in a state in which the specimen S contains water while preventing a situation in which the specimen S dries or freezes. Therefore, it is possible to observe or analyze a water-containing specimen in a state close to the original state by utilizing the charged particle beam device 1000.

Although an example in which the charged particle beam device 1000 is a scanning electron microscope that includes an energy-dispersive radiation detector has been described above, the charged particle beam device 1000 according to the invention is not limited thereto. For example, the charged particle beam device 1000 may be an electron probe microanalyzer (EPMA).

5. Fifth Embodiment

5.1. Charged Particle Beam Device

Figure 20:
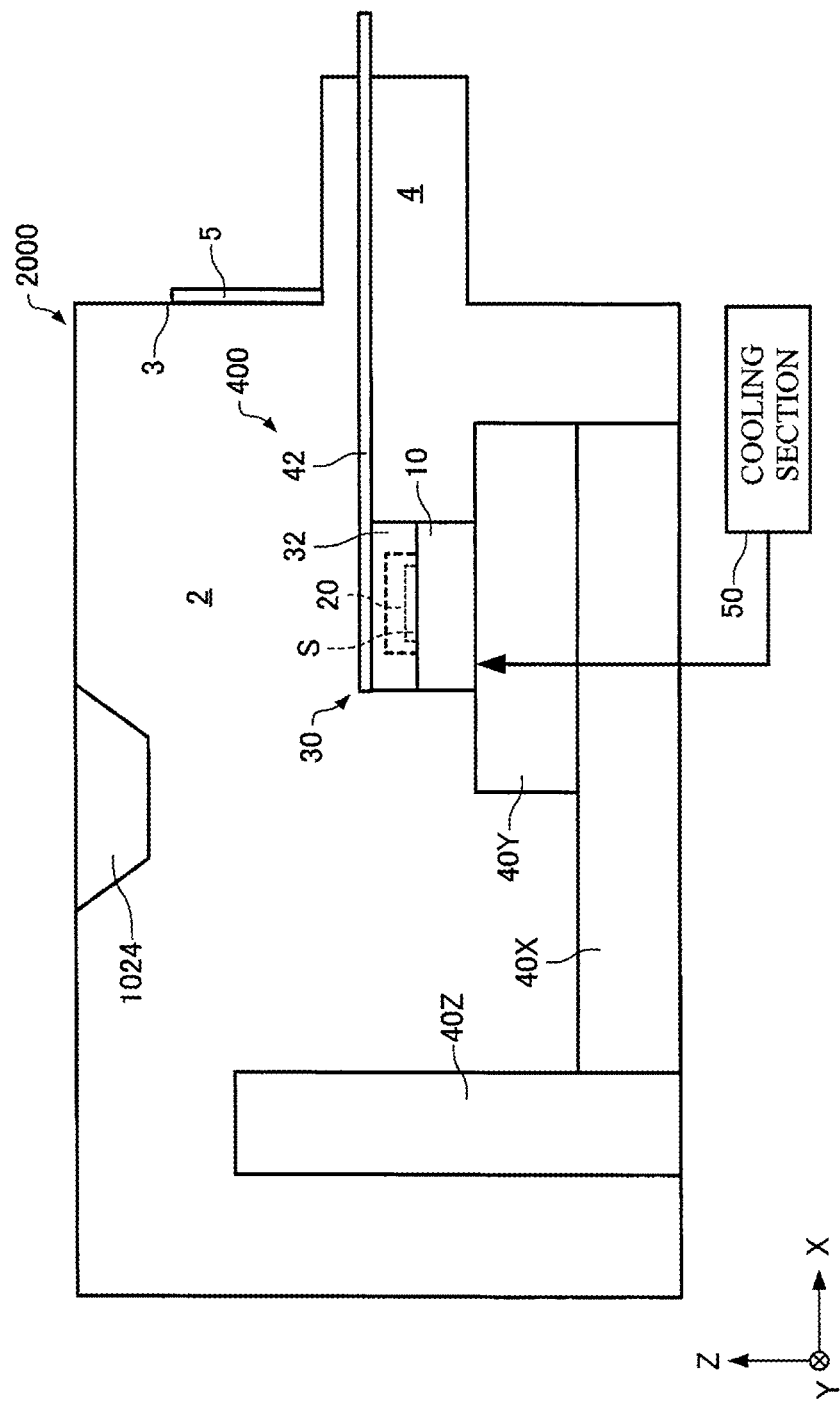
FIG. 20 is a schematic view illustrating the main part of a charged particle beam device according to the fifth embodiment.

A charged particle beam device according to a fifth embodiment of the invention is described below with reference to the drawings. FIG. 20 is a schematic view illustrating the main part of a charged particle beam device 2000 according to the fifth embodiment. The following description focuses on the differences from the specimen stage 100 and the charged particle beam device 1000 described above, and description of the same features is omitted.

As illustrated in FIG. 20, the charged particle beam device 2000 includes a specimen stage 400 and a water retention material chamber 4.

The water retention material chamber 4 is a space for holding the water retention material 20. The water retention material chamber 4 is connected to the specimen chamber 2 through a gate valve 5. The water retention material chamber 4 communicates with the specimen chamber 2 when the gate valve 5 is opened, and forms a closed space when the gate valve 5 is closed. The water retention material chamber 4 can airtightly hold the water retention material 20 that is held by the water retention material holder 32. The water retention material 20 can be saved from the specimen chamber 2 by placing the water retention material 20 in the water retention material chamber 4.

The specimen stage 400 includes a holder moving mechanism 42. As illustrated in FIG. 20, the holder moving mechanism 42 includes a rod that extends from the outside into the water retention material chamber 4 and the specimen chamber 2. The water retention material holder 32 is connected to the end of the rod. The water retention material holder 32 can be moved from the specimen chamber 2 to the water retention material chamber 4, or moved from the water retention material chamber 4 to the specimen chamber 2, by externally operating the rod. Note that the configuration of the holder moving mechanism 42 is not particularly limited as long as the water retention material holder 32 can be moved from the specimen chamber 2 to the water retention material chamber 4, or moved from the water retention material chamber 4 to the specimen chamber 2.

5.2. Specimen Loading Method

Figure 21:
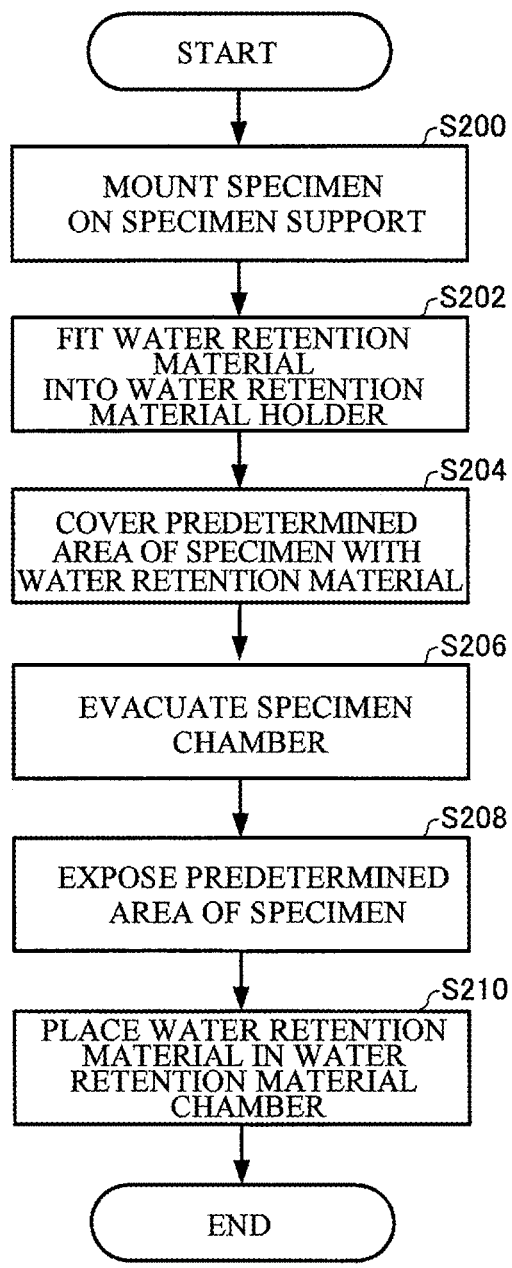
FIG. 21 is a flowchart illustrating an example of a specimen loading method that utilizes a charged particle beam device according to the fifth embodiment.

A specimen loading method that utilizes the charged particle beam device 2000 according to the fifth embodiment is described below with reference to the drawings. FIG. 21 is a flowchart illustrating an example of the specimen loading method that utilizes the charged particle beam device 2000 according to the fifth embodiment. FIGS. 22 to 25 are schematic views illustrating a specimen loading step that utilizes the charged particle beam device 2000.

Figure 22:
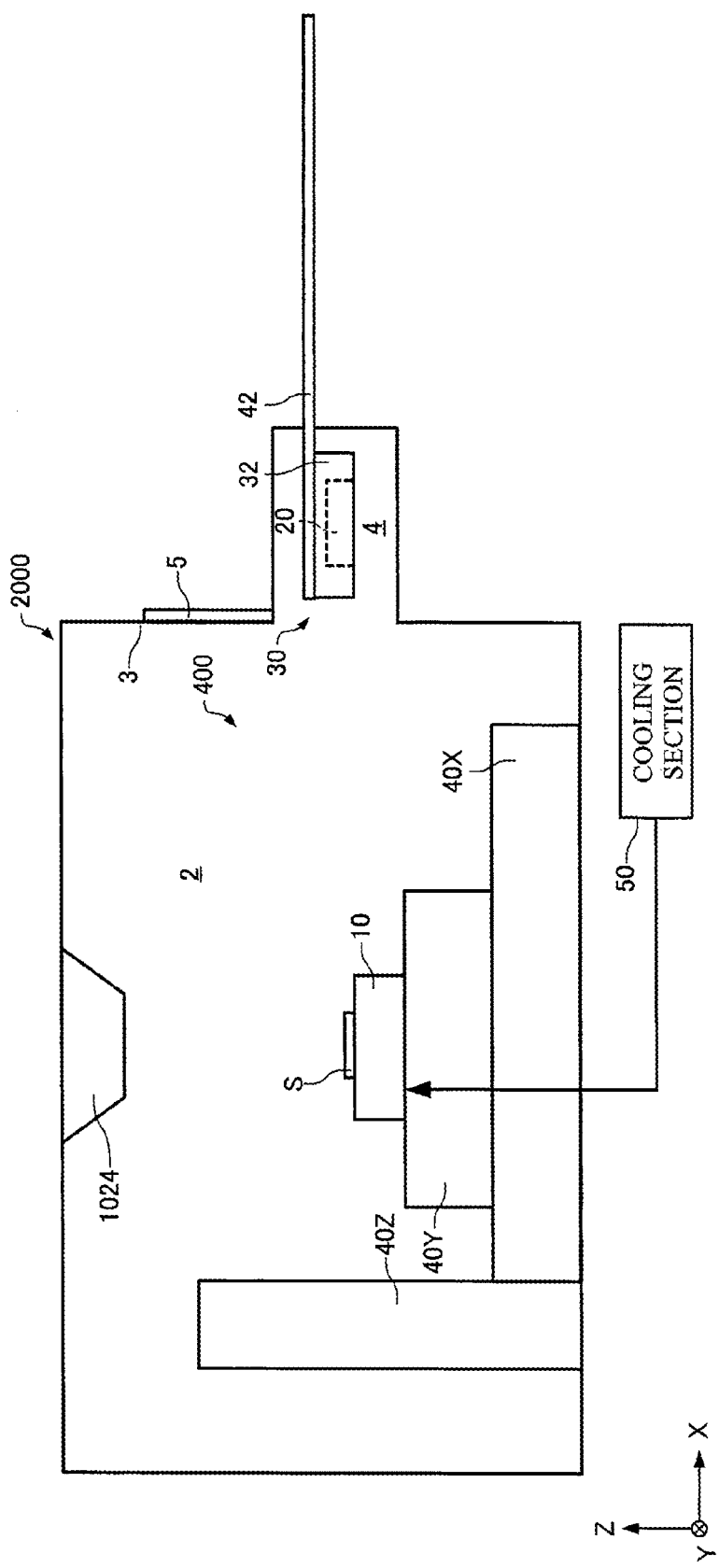
FIG. 22 is a schematic view illustrating a specimen loading step that utilizes a charged particle beam device according to the fifth embodiment.

As illustrated in FIG. 22, the specimen S is mounted on the specimen support 10 (step S200). The specimen S is mounted on the specimen support 10 in a state in which the specimen chamber 2 and the water retention material chamber 4 are set to atmospheric pressure. The specimen support 10 has been cooled to about 0° C. to about 1° C. using the cooling section 50. The specimen S supported on the specimen support 10 is thus cooled.

The water retention material 20 is fitted into the water retention material holder 32, and the water retention material holder 32 (into which the water retention material 20 is fitted) is secured on the holder moving mechanism 42 (rod) (step S202).

Figure 23:
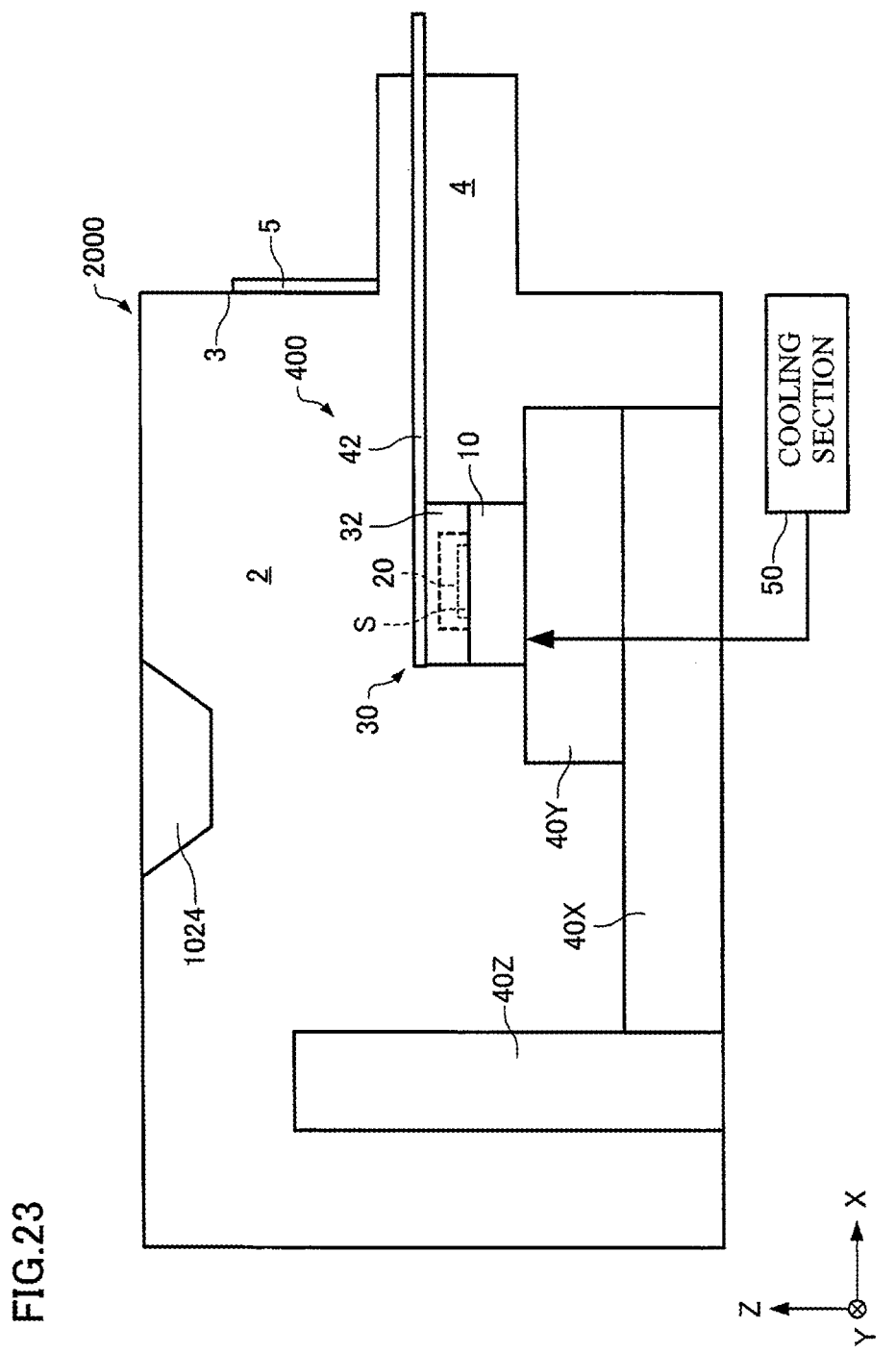
FIG. 23 is a schematic view illustrating a specimen loading step that utilizes a charged particle beam device according to the fifth embodiment.

As illustrated in FIG. 23, the upper surface and the side surface (predetermined area) of the specimen S are covered with the water retention material 20 (step S204). In the example illustrated in FIG. 23, the specimen S is moved to a position within the movable range of the water retention material holder 32 using the stage moving mechanisms 40X, 40Y, and 40Z, and the water retention material 20 is moved to a position over the specimen S using the holder moving mechanism 42 to cover the specimen S with the water retention material 20. In the step S204, the area of the specimen S (i.e., the upper surface and the side surface of the specimen S) that is exposed in a state in which the specimen S is mounted on the specimen support 10 is covered with the water retention material 20.

The specimen chamber 2 is then evacuated (step S206). The specimen chamber 2 is evacuated using the evacuation device that is connected to the specimen chamber 2. The specimen chamber 2 is evacuated using the evacuation device so that the pressure inside the specimen chamber 2 is stably maintained at about 650 Pa. In this case, the gate valve 5 has been opened, and the water retention material chamber 4 is also evacuated.

The step S206 that evacuates the specimen chamber 2 is performed in a state in which the upper surface and the side surface of the specimen S are covered with the water retention material 20. This makes it possible to reduce evaporation of water from the specimen S. Therefore, it is possible to prevent a situation in which the specimen S dries. It is also possible to prevent a situation in which the specimen S freezes due to heat of evaporation. The specimen S has been cooled to 0° C. to 1° C. Therefore, it is possible to keep the water contained in the specimen S in a liquid phase even when the pressure inside the specimen chamber 2 has reached 650 Pa.

Figure 24:
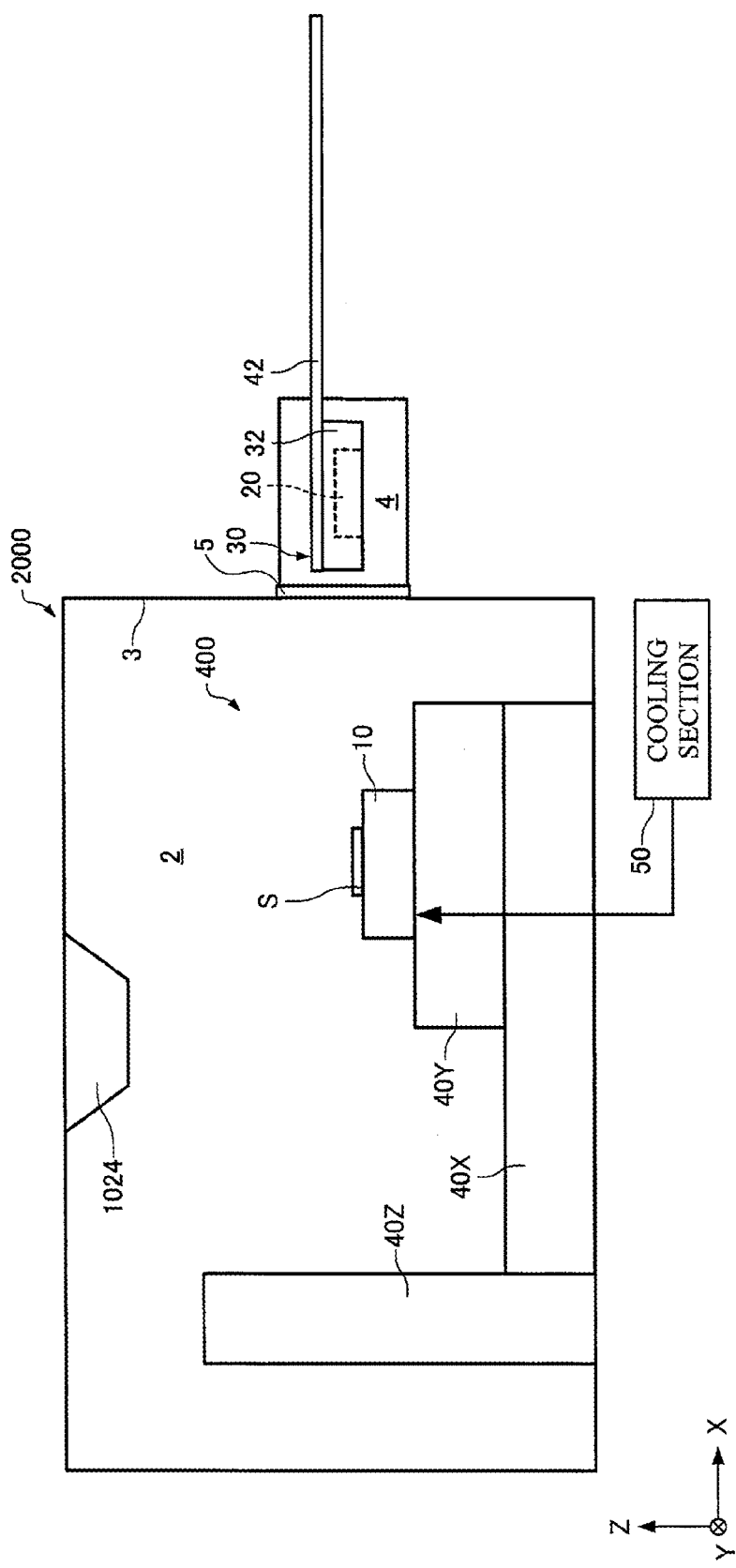
FIG. 24 is a schematic view illustrating a specimen loading step that utilizes a charged particle beam device according to the fifth embodiment.

As illustrated in FIG. 24, the upper surface and the side surface (predetermined area) of the specimen S that is covered with the water retention material 20 are exposed (step S208), and the water retention material 20 is placed in the water retention material chamber 4 (step S210).

More specifically, the upper surface and the side surface of the specimen S are exposed by moving the water retention material 20 (that covers the specimen S) by operating the holder moving mechanism 42. The water retention material 20 is then moved to the water retention material chamber 4. The gate valve 5 is then closed so that the water retention material 20 is held within the water retention material chamber 4. It is possible to prevent a situation in which water that has evaporated from the water retention material 20 is supplied to the specimen S, by placing the water retention material 20 in the water retention material chamber 4.

The specimen S can thus be loaded into the specimen chamber 2.

After the upper surface and the side surface of the specimen S have been exposed, an electron beam is applied to the upper surface of the specimen S. It is possible to implement SEM observation or elemental analysis by detecting secondary electrons or characteristic X-rays generated (emitted or released) from the specimen S.

Note that water that has evaporated from the specimen S can be supplied to the specimen S by opening the gate valve 5 after the step S210. Specifically, the charged particle beam device 2000 is configured so that the water content in the specimen S can be adjusted by opening or closing the gate valve 5 even in a state in which the specimen chamber 2 is maintained under a specific pressure. Therefore, it is possible to optionally supply water to the specimen S during observation or analysis.

Figure 25:
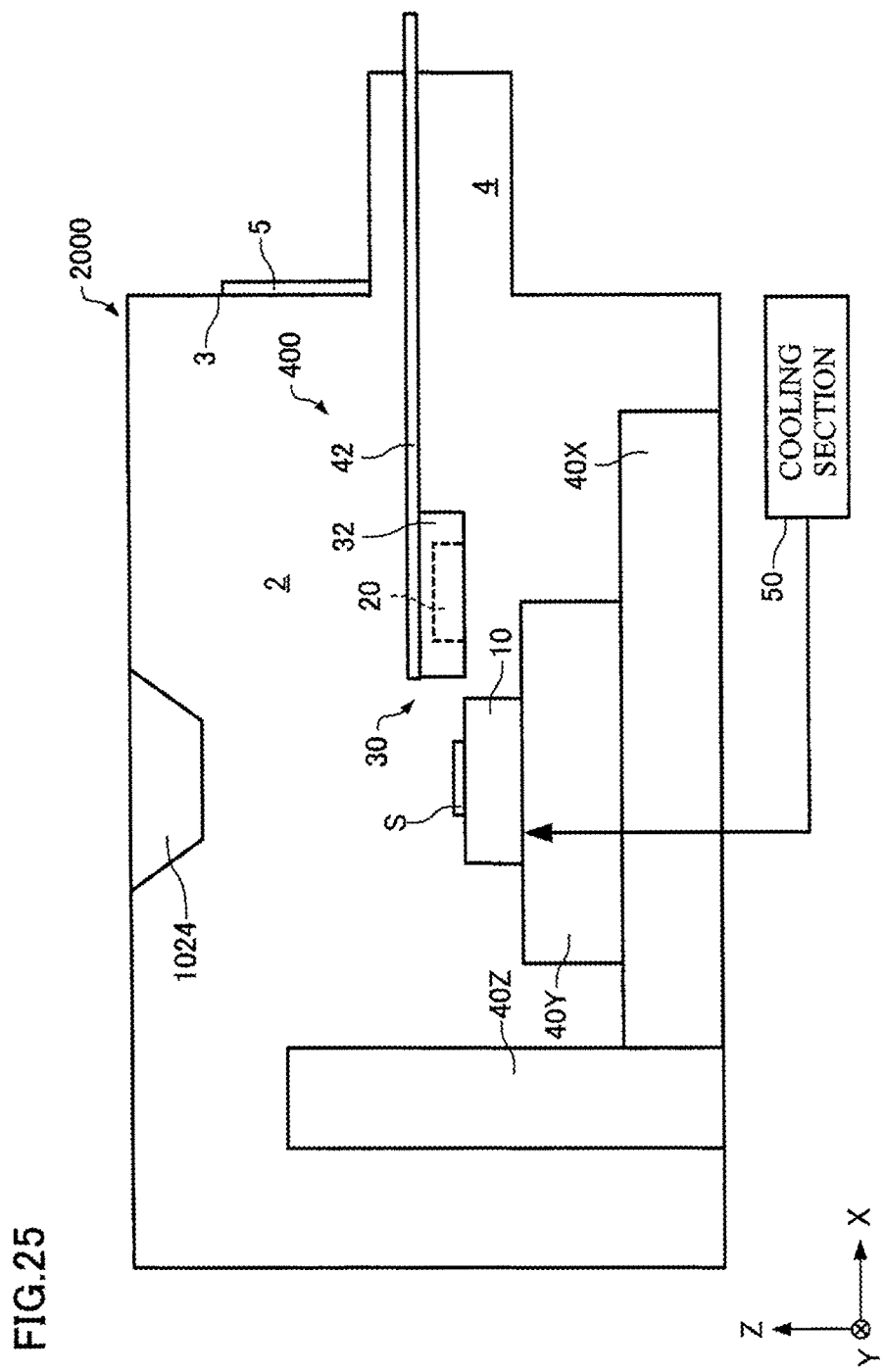
FIG. 25 is a schematic view illustrating a specimen loading step that utilizes a charged particle beam device according to the fifth embodiment.

The amount of water supplied to the specimen S per unit time can be increased as compared with the case where the gate valve 5 is merely opened (in a state in which the water retention material 20 is placed in the water retention material chamber 4), for example, by placing the water retention material 20 at a position near the specimen S using the holder moving mechanism 42 after opening the gate valve 5 (see FIG. 25).

Since the charged particle beam device 2000 includes the water retention material chamber 4 that is connected to the specimen chamber 2 (into which the specimen S is loaded) through the gate valve 5, and can hold the water retention material 20, it is possible to prevent a situation in which water that has evaporated from the water retention material 20 is supplied to the specimen S during observation or analysis. According to the charged particle beam device 2000, it is possible to supply water to the specimen S at the desired timing, and adjust the amount of water supplied to the specimen S by operating the gate valve 5. According to the charged particle beam device 2000, it is possible to reduce damage to the evacuation device that may occur when water from the water retention material 20 is discharged.

Since the specimen loading method that utilizes the charged particle beam device 2000 includes the step that places the water retention material 20 in the water retention material chamber 4 that is connected to the specimen chamber 2 through the gate valve 5 (step S210), it is possible to prevent a situation in which water that has evaporated from the water retention material 20 is supplied to the specimen S during observation or analysis. It is also possible to reduce damage to the evacuation device that may occur when water from the water retention material 20 is discharged.

Since the specimen loading method that utilizes the charged particle beam device 2000 includes the step that moves the water retention material 20 from the water retention material chamber 4 to the specimen chamber 2, and supplies water that has evaporated from the water retention material 20 to the specimen S, it is possible to supply water to the specimen S during observation or analysis.

5.3. Modification

Figure 26:
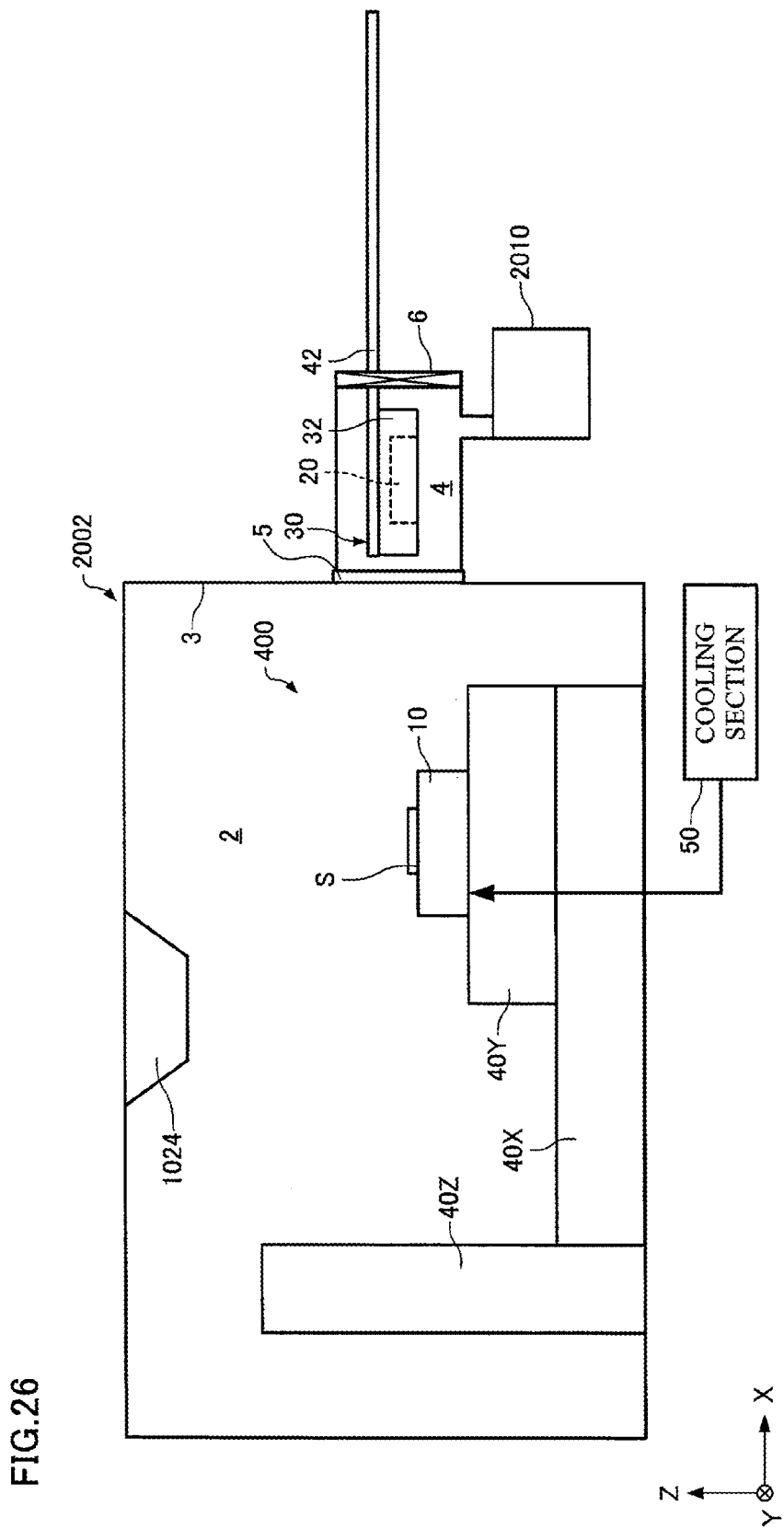
FIG. 26 is a schematic view illustrating the configuration of a charged particle beam device according to a modification of the fifth embodiment.

A charged particle beam device according to a modification of the fifth embodiment is described below with reference to the drawings. FIG. 26 is a schematic view illustrating the configuration of a charged particle beam device 2002 according to the modification of the fifth embodiment. Note that the members of the charged particle beam device 2002 according to the modification of the fifth embodiment that have the same functions as those of the charged particle beam device 2000 described above are indicated by the same reference signs (symbols), and detailed description thereof is omitted.

As illustrated in FIG. 26, the charged particle beam device 2002 includes an evacuation device 2010 that evacuates the water retention material chamber 4. According to the charged particle beam device 2002, the water retention material chamber 4 can be evacuated independently of the specimen chamber 2 by utilizing the evacuation device 2010.

The charged particle beam device 2002 has a configuration in which a door 6 for removing the water retention material 20 is provided to the water retention material chamber 4.

Since the charged particle beam device 2002 includes the evacuation device 2010 that evacuates the water retention material chamber 4, it is possible to exchange the water retention material 20, or supply water to the water retention material 20 in a state in which the specimen chamber 2 is maintained under a specific pressure (e.g., 650 Pa).

The water retention material 20 may be exchanged using the charged particle beam device 2002 as described below, for example. The water retention material 20 that has been placed in the specimen chamber 2 (that has been evacuated using the evacuation device, and maintained under a specific pressure) is moved to the water retention material chamber 4. The gate valve 5 is closed so that the water retention material 20 is held within the water retention material chamber 4. After opening the water retention material chamber 4 to the atmosphere, the door 6 is opened, and the water retention material 20 is removed. After exchanging the water retention material 20 (e.g., after supplying water to the water retention material 20), the water retention material 20 is placed in the water retention material chamber 4. The water retention material chamber 4 in which the water retention material 20 is placed is evacuated using the evacuation device 2010, and the gate valve 5 is opened to introduce the water retention material 20 into the specimen chamber 2.

6. Sixth Embodiment

Figure 27:
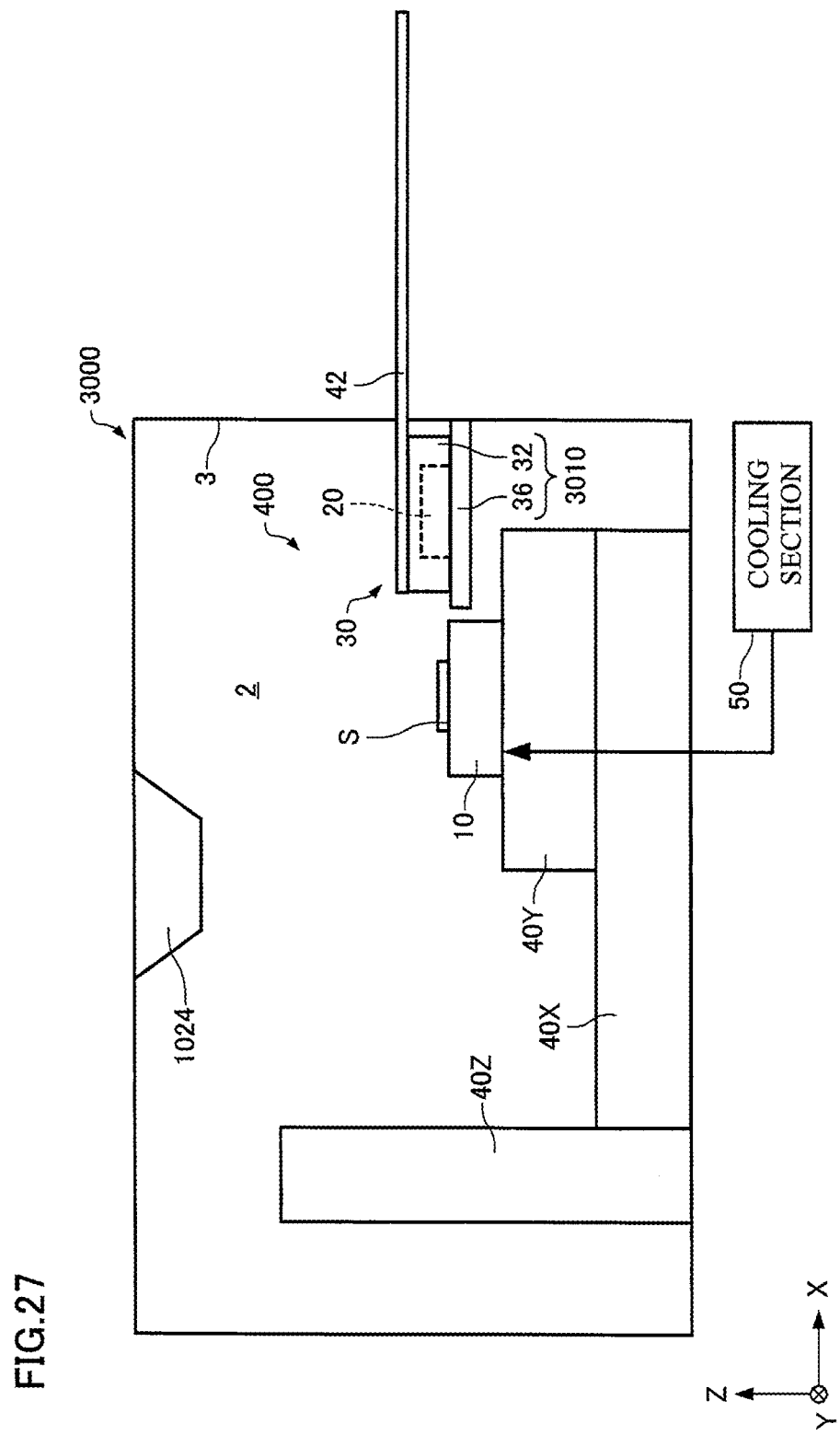
FIG. 27 is a schematic view illustrating the main part of a charged particle beam device according to the sixth embodiment.

A charged particle beam device according to a sixth embodiment of the invention is described below with reference to the drawings. FIG. 27 is a schematic view illustrating the main part of a charged particle beam device 3000 according to the sixth embodiment. Note that the following description focuses on the differences from the specimen stages 100 and 400 and the charged particle beam devices 1000 and 2000 described above, and description of the same features is omitted.

The charged particle beam device 2000 described above is configured to prevent a situation in which water that has evaporated from the water retention material 20 is supplied to the specimen S, by placing the water retention material 20 in the water retention material chamber 4 (see FIG. 24).

As illustrated in FIG. 27, the charged particle beam device 3000 is configured to prevent a situation in which water that has evaporated from the water retention material 20 is supplied to the specimen S, by placing the water retention material 20 in a container 3010.

The container 3010 includes the water retention material holder 32 and a lid member 36. The lid member 36 is connected to (secured on) the wall 3. The lid member 36 forms the container 3010 that airtightly holds the water retention material 20 together with the water retention material holder 32. In the example illustrated in FIG. 27, the lid member 36 is a plate-like member, and is configured to close the recess formed in the water retention material holder 32 when the water retention material holder 32 is placed on the lid member 36. Therefore, the container 3010 can airtightly hold the water retention material 20. Note that the configuration of the container 3010 is not particularly limited as long as the container 3010 can airtightly hold the water retention material 20.

Figure 28:
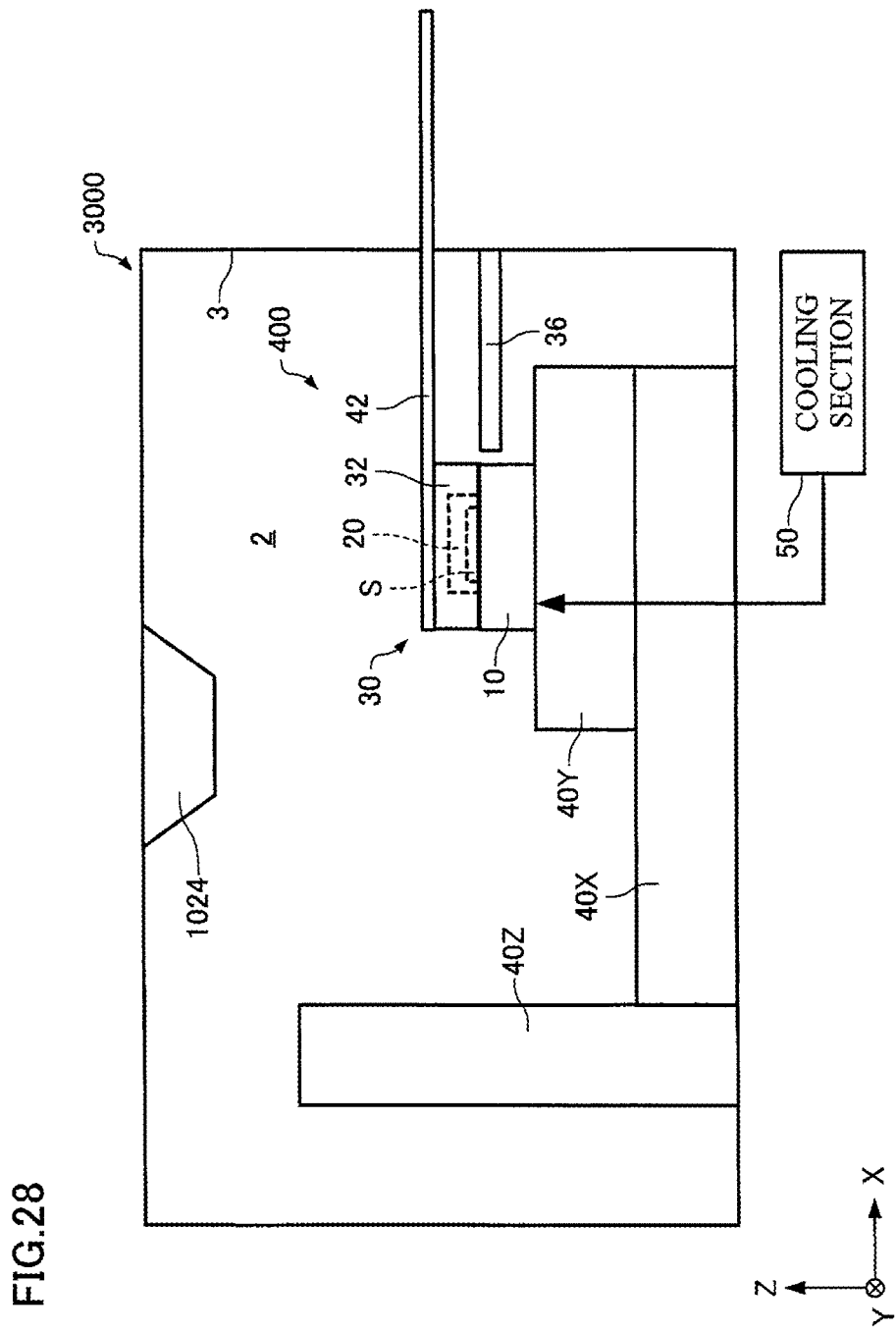
FIG. 28 is a schematic view illustrating the main part of a charged particle beam device according to the sixth embodiment.

FIG. 28 is a schematic view illustrating the main part of the charged particle beam device 3000. FIG. 28 illustrates a state in which the specimen S is covered with the water retention material 20.

The charged particle beam device 3000 is configured so that the water retention material 20 can be placed in the container 3010 (see FIG. 27), and the specimen S can be covered with the water retention material 20 (see FIG. 28) by moving the water retention material 20 by operating the holder moving mechanism 42.

Although FIG. 27 illustrates an example in which the lid member 36 is placed so as to close the entirety of the opening of the recess formed in the water retention material holder 32, the lid member 36 may be placed so as to close part of the opening of the recess formed in the water retention material holder 32. It is possible to adjust the amount of water that evaporates from the water retention material 20 and is supplied to the specimen S by adjusting the degree by which the lid member 36 closes the opening of the recess formed in the water retention material holder 32.

A specimen loading method that utilizes the charged particle beam device 3000 differs from the specimen loading method that utilizes the charged particle beam device 2000 (see FIG. 21) as to the step S210. Specifically, while the specimen loading method that utilizes the charged particle beam device 2000 places the water retention material 20 in the water retention material chamber 4 in the step S210, the specimen loading method that utilizes the charged particle beam device 3000 places the water retention material 20 in the container 3010 within the specimen chamber 2 in the step S210. The remaining steps of the specimen loading method that utilizes the charged particle beam device 3000 are the same as those of the specimen loading method that utilizes the charged particle beam device 2000 (see FIG. 21), and description thereof is omitted.

Since the specimen loading method that utilizes the charged particle beam device 3000 includes the step that places the water retention material 20 in the container 3010 within the specimen chamber 2 after the step that exposes the predetermined area of the specimen S that is covered with the water retention material 20, it is possible to prevent a situation in which water that has evaporated from the water retention material 20 is supplied to the specimen S during observation or analysis. It is also possible to reduce damage to the evacuation device that may occur when water from the water retention material 20 is discharged.

6.2. Modification

Figure 29:
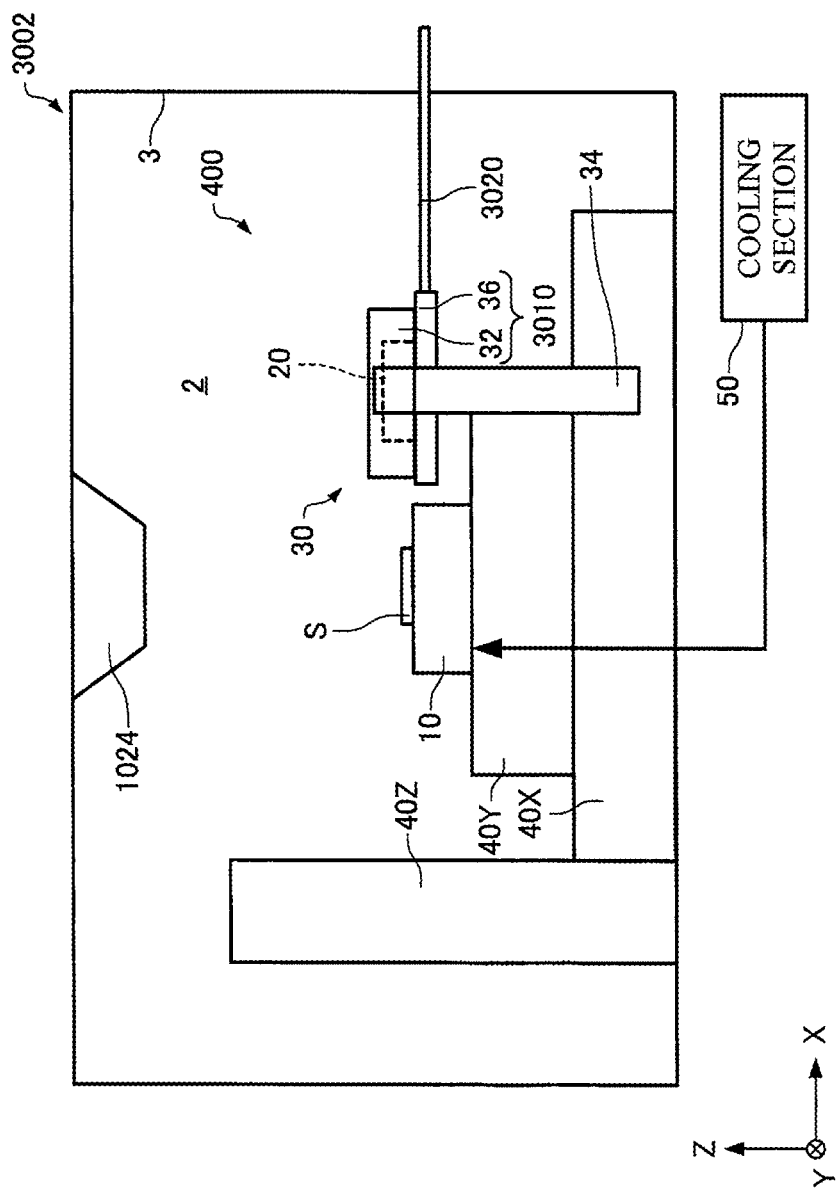
FIG. 29 is a schematic view illustrating the configuration of a charged particle beam device according to a modification of the sixth embodiment.
Figure 30:
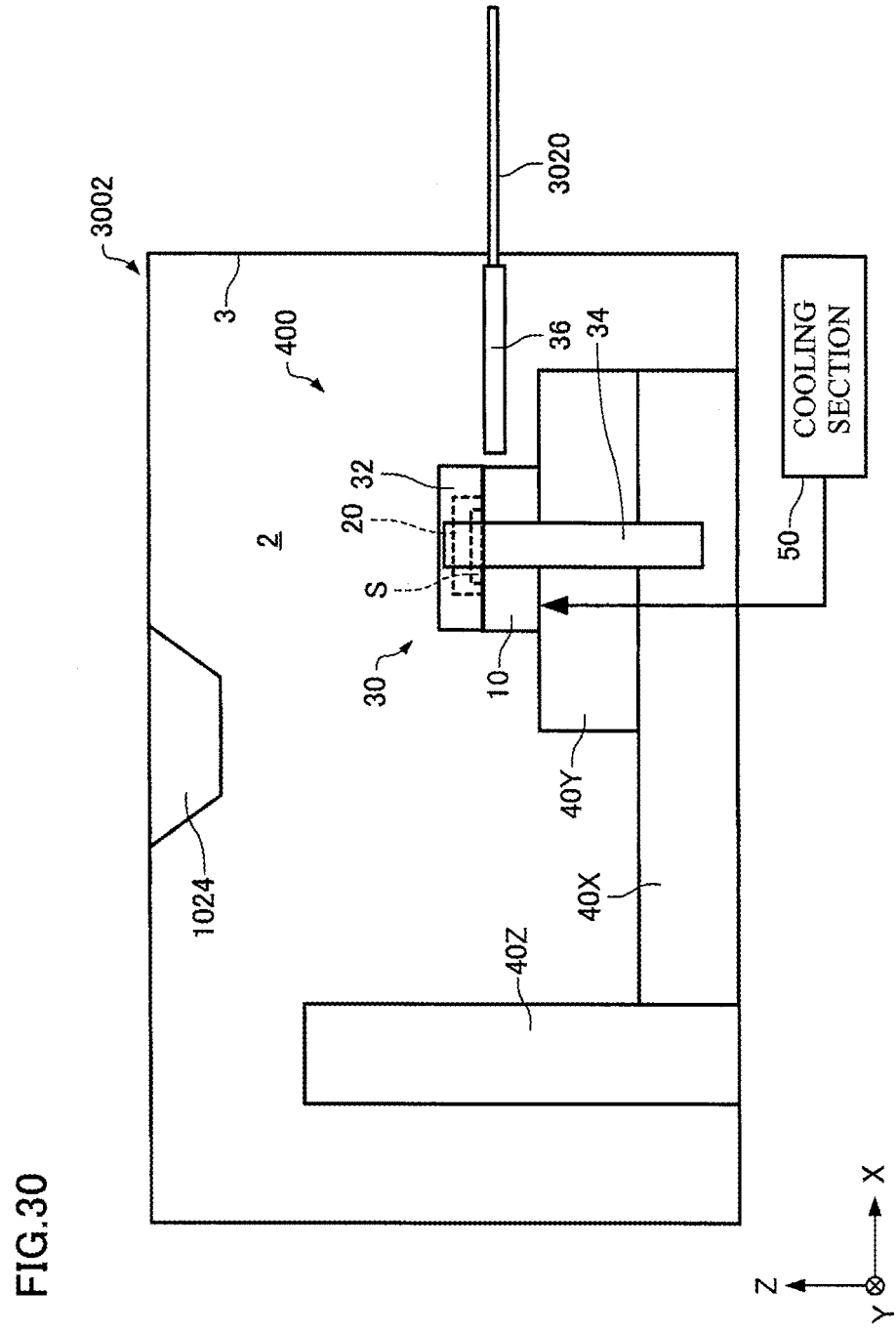
FIG. 30 is a schematic view illustrating the configuration of a charged particle beam device according to a modification of the sixth embodiment.

A charged particle beam device according to a modification of the sixth embodiment is described below with reference to the drawings. FIGS. 29 and 30 are schematic views illustrating the configuration of a charged particle beam device 3002 according to the modification of the sixth embodiment. Note that FIG. 29 illustrates a state in which the water retention material 20 is placed in the container 3010, and FIG. 30 illustrates a state in which the specimen S is covered with the water retention material 20. The members of the charged particle beam device 3002 according to the modification of the sixth embodiment that have the same functions as those of the charged particle beam device 3000 described above are indicated by the same reference signs (symbols), and detailed description thereof is omitted.

The charged particle beam device 3000 is configured so that the water retention material 20 is placed in the container 3010, and the specimen S is covered with the water retention material 20 by moving the water retention material 20 by operating the holder moving mechanism 42 (see FIGS. 27 and 28).

As illustrated in FIGS. 29 and 30, the charged particle beam device 3002 is configured so that the water retention material 20 can be placed in the container 3010, and the specimen S can be covered with the water retention material 20 by moving the lid member 36 by operating a lid member moving mechanism 3020.

The lid member moving mechanism 3020 moves the lid member 36 within the specimen chamber 2. The lid member moving mechanism 3020 includes a rod that extends from the outside into the specimen chamber 2, for example. The lid member 36 is connected to the end of the rod. The lid member 36 can be moved by externally operating the rod. Note that the configuration of the lid member moving mechanism 3020 is not particularly limited as long as the lid member moving mechanism 3020 can move the lid member 36 within the specimen chamber 2.

The water retention material holder 32 is immobilized by the holder support member 34.

According to the charged particle beam device 3002, the water retention material 20 can be placed in the container 3010 (see FIG. 29), and the specimen S can be covered with the water retention material 20 (see FIG. 30) by moving the lid member 36 by operating the lid member moving mechanism 3020.

The charged particle beam device 3002 and the specimen loading method that utilizes the charged particle beam device 3002 can achieve the same advantageous effects as those achieved by the charged particle beam device 3000 and the specimen loading method that utilizes the charged particle beam device 3000.

The invention includes configurations that are substantially the same (e.g., in function, method and effects, or object and effects) as the configurations described above in connection with the embodiments. The invention also includes a configuration in which an unsubstantial element described above in connection with the embodiments is replaced by another element. The invention also includes a configuration having the same effects as those of the configurations described above in connection with the embodiments, or a configuration capable of achieving the same object as those of the configurations described above in connection with the embodiments. The invention further includes a configuration obtained by adding known technology to the configurations described above in connection with the embodiments.

REFERENCE SIGNS LIST

2: specimen chamber, 3: wall, 4: water retention material chamber, 5: gate valve, 6: door, 10: specimen support, 20:

water retention material, 30: holder, 32: water retention material holder, 34: holder support member, 36: lid member, 40X: X moving mechanism, 40Y: Y moving mechanism, 40Z: Z moving mechanism, 42: holder moving mechanism, 50: cooling section, 100, 102, 200: specimen stage, 210: restriction section, 300: specimen stage, 310: manipulator, 400: specimen stage, 1000: charged particle beam device, 1010: electron beam source, 1020: optical system, 1022: condenser lens, 1024: objective lens, 1024a: coil, 1024b: yoke, 1024c: pole piece, 1030: scanning deflector, 1040: secondary electron detector, 1050: radiation detector, 2000, 2002: charged particle beam device, 2010: evacuation device, 3000, 3002: charged particle beam device, 3010: container, 3020: lid member moving mechanism

The invention claimed is:

1. A specimen loading method for loading a specimen that contains water into a specimen chamber of a charged particle beam device, the specimen loading method comprising:
   a step of mounting the specimen on a specimen support;
   a step of covering a predetermined area of the specimen with a water retention material;
   a step of evacuating the specimen chamber in which the specimen having the predetermined area covered with the water retention material is placed; and
   a step of exposing the predetermined area covered with the water retention material,
   wherein the step of exposing the predetermined area includes exposing the predetermined area by moving the specimen and the water retention material relative to each other.

2. The specimen loading method as defined in claim 1, wherein the step of exposing the predetermined area includes exposing the predetermined area by moving the specimen support.

3. The specimen loading method as defined in claim 1, wherein the step of exposing the predetermined area includes exposing the predetermined area by moving the water retention material.

4. The specimen loading method as defined in claim 1, wherein the step of evacuating the specimen chamber includes cooling the specimen.

5. The specimen loading method as defined in claim 1, further comprising:
   a step of placing the water retention material in a water retention material chamber that is connected to the specimen chamber through a gate valve, after the step of exposing the predetermined area.

6. The specimen loading method as defined in claim 5, further comprising:
   a step of moving the water retention material from the water retention material chamber to the specimen chamber, and evaporating water from the water retention material in the specimen chamber to supply the water to the specimen.

7. The specimen loading method as defined in claim 1, further comprising:
   a step of placing the water retention material in a container within the specimen chamber, after the step of exposing the predetermined area.

8. A specimen stage that is used for a charged particle beam device, the specimen stage comprising:
   a specimen support that supports a specimen;
   a holder that can hold a water retention material that covers a predetermined area of the specimen; and
   a moving mechanism that moves the specimen support or the holder exposing the predetermined area by moving the specimen and the water retention material relative to each other.

9. A specimen stage that is used for a charged particle beam device, the specimen stage comprising:
   a specimen support that supports a specimen;
   a moving mechanism that moves the specimen support; and
   a restriction section that restricts movement of a water retention material along with movement of the specimen support, the water retention material covering a predetermined area of the specimen, the movement of the specimen support exposing the predetermined area by moving the specimen relative to the water retention material.

10. A charged particle beam device comprising:
    a specimen stage having a specimen support that supports a specimen;
    a holder that can hold a water retention material that covers a predetermined area of the specimen;
    a moving mechanism that moves the specimen support or the holder; and
    a water retention material chamber that is connected to a specimen chamber through a gate valve, and can hold the water retention material, the specimen being loaded into the specimen chamber.

11. A charged particle beam device comprising:
    a specimen stage having a specimen support that supports a specimen;
    a moving mechanism that moves the specimen support;
    a restriction section that restricts movement of a water retention material along with movement of the specimen support, the water retention material covering a predetermined area of the specimen; and
    a water retention material chamber that is connected to a specimen chamber through a gate valve, and can hold the water retention material, the specimen being loaded into the specimen chamber.

* * * * *